United States Patent
Mak et al.

(10) Patent No.: US 11,116,579 B2
(45) Date of Patent: Sep. 14, 2021

(54) INTRAOPERATIVE MEDICAL IMAGING METHOD AND SYSTEM

(71) Applicant: SYNAPTIVE MEDICAL INC., Toronto (CA)

(72) Inventors: Siu Wai Jacky Mak, Toronto (CA); Arun Victor Jagga, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 518 days.

(21) Appl. No.: 15/573,279

(22) PCT Filed: Jun. 27, 2016

(86) PCT No.: PCT/CA2016/000176
§ 371 (c)(1),
(2) Date: May 14, 2018

(87) PCT Pub. No.: WO2018/000071
PCT Pub. Date: Jan. 4, 2018

(65) Prior Publication Data
US 2018/0325601 A1    Nov. 15, 2018

(51) Int. Cl.
*A61B 34/20* (2016.01)
*A61B 34/10* (2016.01)
(Continued)

(52) U.S. Cl.
CPC .............. *A61B 34/20* (2016.02); *A61B 5/00* (2013.01); *A61B 5/0035* (2013.01);
(Continued)

(58) Field of Classification Search
CPC ... A61B 34/20; A61B 34/10; A61B 2034/105; A61B 2034/2055; A61B 2034/2057;
(Continued)

(56) References Cited

U.S. PATENT DOCUMENTS 8,208,719 B2    6/2012    Gordon et al.
2002/0077546 A1    6/2002    Aldefeld et al.
(Continued)

FOREIGN PATENT DOCUMENTS

WO    WO2013157006 A1    10/2013
WO    WO-2014139022 A1 *  9/2014    ......... A61B 5/14539

OTHER PUBLICATIONS

PCT International Search Report, dated Mar. 27, 2017, PCT/CA2016/000176.
(Continued)

*Primary Examiner* — Amelie R Davis
*Assistant Examiner* — John Denny Li

(57) ABSTRACT

Methods and apparatus is provided for use in a medical procedure for image acquisition using a high-resolution imaging system, a three dimensional imaging system and a navigation system. A 3D imaging scan of an imaged portion of the surface of the patient is acquired using the three dimensional imaging system. Then, a first high-resolution imaging scan covering a first sub-portion of the imaged portion is acquired using the high-resolution imaging system, which is tracked by the navigation system. The 3D imaging scan and the first high-resolution imaging scan are combined to create an enhanced three dimensional image having contour lines to provide a visual representation of depth derived from depth information acquired from both the three dimensional imaging system and the high-resolution imaging system. Subsequent high resolution scans may then be stitched into the image and the updated image displayed in real-time.

20 Claims, 15 Drawing Sheets

(51) Int. Cl.

| | | |
|---|---|---|
| *A61B 5/00* | (2006.01) | |
| *G06T 7/30* | (2017.01) | |
| *G06T 15/00* | (2011.01) | |
| *A61B 5/06* | (2006.01) | |
| *A61B 5/055* | (2006.01) | |
| *A61B 90/00* | (2016.01) | |

(52) U.S. Cl.
CPC .......... *A61B 5/0042* (2013.01); *A61B 5/0066* (2013.01); *A61B 5/0084* (2013.01); *A61B 34/10* (2016.02); *G06T 7/30* (2017.01); *G06T 15/00* (2013.01); *A61B 5/0064* (2013.01); *A61B 5/055* (2013.01); *A61B 5/064* (2013.01); *A61B 2034/105* (2016.02); *A61B 2034/2055* (2016.02); *A61B 2034/2057* (2016.02); *A61B 2034/2065* (2016.02); *A61B 2090/367* (2016.02); *A61B 2090/3735* (2016.02); *A61B 2505/05* (2013.01); *A61B 2576/00* (2013.01); *A61B 2576/026* (2013.01); *G06T 2207/10028* (2013.01); *G06T 2207/10101* (2013.01); *G06T 2207/20221* (2013.01)

(58) Field of Classification Search
CPC ...... A61B 2034/2065; A61B 2090/367; A61B 2090/3735; A61B 5/0064; A61B 5/055; A61B 5/064; A61B 5/0066; A61B 5/0084; A61B 5/0042; A61B 5/0035; A61B 5/00; A61B 2505/05; A61B 2576/00; A61B 2576/026; G06T 7/30; G06T 15/00; G06T 2207/10028; G06T 2207/10101; G06T 2207/20221
See application file for complete search history.

(56) References Cited

U.S. PATENT DOCUMENTS

| | | | | |
|---|---|---|---|---|
| 2003/0076925 | A1* | 4/2003 | DeSilets | A61B 8/5238 378/63 |
| 2011/0106102 | A1 | 5/2011 | Balicki et al. | |
| 2012/0184846 | A1 | 7/2012 | Izatt et al. | |
| 2012/0197112 | A1 | 8/2012 | McNichols | |
| 2014/0221822 | A1 | 8/2014 | Ehlers et al. | |
| 2014/0270445 | A1 | 9/2014 | Kemp | |
| 2016/0040976 | A1* | 2/2016 | Berkeley | G01N 21/4795 356/479 |
| 2018/0116728 | A1* | 5/2018 | Lang | A61B 17/1742 |
| 2020/0005552 | A1* | 1/2020 | Furst | G06T 7/344 |

OTHER PUBLICATIONS

Adler et al., "Three-dimensional optical coherence tomography of Barrett's esophagus and buried glands beneath neo-squamous epithelium following radiofrequency ablation", Endoscopy. Sep. 2009 41(9), pp. 773-776.

Eichel et al., "Automated 3D Reconstruction and Segmentation from Optical Coherence Tomography", ECCV 2010, Part III, LNCS 6313, pp. 44-57.

Ishikawa et al., "Three-Dimensional Optical Coherence Tomography (3D-OCT) Image Enhancement with Segmentation-Free Contour Modeling C-Mode", Investigative Ophthalmology & Visual Science, Mar. 2009, vol. 50, No. 3.

Kang et al., "Real-time three-dimensional Fourierdomain optical coherence tomography video image guided microsurgeries", Journal of Biomedical Optics 17(8), 081403 (Aug. 2012).

Kirtane et al., "Endoscopic Optical Coherence Tomography (OCT): Advances in Gastrointestinal Imaging", Hindawi Publishing Corporation Gastroenterology Research and Practice vol. 2014, Article ID 376367.

Izatt et al., "High-resolution endoscopic imaging of the GI tract using optical coherence tomography", Gastrointestinal Endoscopy, May 2000.

Tsai et al, "Endoscopic Optical Coherence Tomography for Clinical Gastroenterology", Diagnostics 2014, 4, pp. 57-93.

Wojtkowski et al., "Three-dimensional Retinal Imaging with High-Speed Ultrahigh-Resolution Optical Coherence Tomography", Ophthalmology. Oct. 2005 ; 112(10): pp. 1734-1746.

* cited by examiner

INTRAOPERATIVE MEDICAL IMAGING METHOD AND SYSTEM

CROSS-REFERENCE TO RELATED APPLICATION(S)

This document is a national phase entry application which claims the benefit of, and priority to, International Patent Application No. PCT/CA2016/000176, filed on May 14, 2018, entitled "INTRAOPERATIVE MEDICAL IMAGING METHOD AND SYSTEM," which herein is incorporated by reference in its entirety.

TECHNICAL FIELD

The subject matter of the present disclosure generally relates to the field of image guided medical procedures. More particularly, the subject matter of the present disclosure technically relates to the field of OCT image stitching in relation to image guided medical procedures. Even more particularly, the subject matter of the present disclosure technically relates to the field of acquiring and applying methods to amalgamate OCT scans to preoperative imaging in relation to image guided medical procedures.

BACKGROUND

In the related art, image-guided surgical procedures typically involve using a surgical instrument, such as a fibre optic scope, an optical coherence tomography (OCT) probe, a micro ultrasound transducer, an electronic sensor or stimulator, or an access port. In the example of a port-based surgery, a surgeon or robotic surgical system may perform or assist in a surgical procedure involving tumor resection. However, in the related art, residual tumor tissue may remain after resection, hopefully minimized; and eliminating the tumour entirely may result in undue trauma to otherwise healthy cerebral tissue. In such related art procedures, undue trauma may occur, for example, due to contact with the access port, stress to the brain matter, unintentional impact with surgical devices, and/or accidental resection of healthy tissue. In the related art, minimizing trauma is a challenge as ensuring that the spatial reference of the patient as accurately and fully understood by the surgical system has technological limitations.

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field. Optical tracking systems, used in the medical procedure, track the position of a part of the instrument that is within line-of-site of the optical tracking camera. These optical tracking systems also require a reference to the patient to know where the instrument is relative to the target (e.g., a tumour) of the medical procedure.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Structured light sensor systems are increasingly being used in a wide array of applications, including medical procedures. These sensor systems determine the shape and/or features of an object positioned in a scene of the sensor system's view. In recent years, many methods have been proposed for implementing structured light modeling systems that are capable of acquiring fast and accurate high resolution structured light images of objects for various applications.

Structured light sensor systems and methods typically have one or more projectors as a light source for projecting onto a surface and one or more cameras at a defined, typically rectified relative position from the projector for imaging the lighted surface. The camera and the projector therefore have different optical paths, and the distance between them is referred to as the baseline. Through knowledge of the baseline distance as well as projection and imaging angles, geometric equations are utilized to determine distance to the imaged object. The main differences among the various triangulation methods known in the art lie in the method of projection as well as the type of light projected, typically structured light, and in the process of image decoding to obtain three dimensional data.

A structured light sensor system may be contemplated as a novel extension of a surgical navigation systems. One popular structured light sensor system is created by Mantis Vision, which utilizes a single frame structured light active system to project infrared light patterns onto an environment. To capture structured light information, a projector overlays an infrared light pattern onto the scanning target. Then a camera system synched to the projector, captures the scene with the light reflected by the object for at least the timeframe of one frame of the structured light scan. The technology works even in complete darkness, since it includes its own illumination; in bright environments the quality of the resulting image depends on the hardware used. Another technology for providing 3D contour information is by combining photometric imaging and geometric imaging such as 3D imager built by a company name Fuel3D™ to produce 3D contour scan images. This technique first acquires a series of stereoscopic 2D photographs with several lighting directions. In particular, photometric imaging is used to acquire color and high frequency 3D detail from the object of interest. Geometric imaging is sued to acquire accurate underlying 3D shape information from the object. Optical localization is used to determine the position of the imaging device during the acquisition process. Data fusion is then performed to combine the data output of the photometric and geometric processes to produce a single 3D image with contour of the object.

During a medical procedure, navigation systems require a registration to transform between the physical position of the patient in the operating room and the volumetric image set (e.g., MRI/CT) being used to navigate. Conventionally, this registration is done relative to the position of a reference tool, which is visible by the tracking system and stays fixed in position and orientation relative to the patient throughout the procedure.

This registration is typically accomplished through correspondence touch points (e.g., either fiducial or anatomic points). Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position. Another conventional approach to collecting the touch points includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask, which requires a high level of operator training and is operator dependent. This approach also provides only a limited number of points.

Other common limitations of the conventional approaches to registration discussed above include a stylus that needs to remain visible to the tracking system, which may not necessarily be possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult to be completed again during the surgical procedure.

In the related art, the use of many registration devices and methods may result in undue damage to the cerebral tissue, thereby contributing to the loss of long-distance axonal connections. Although cell replacement and axonal pathfinding strategies are often explored independently in the related art, no related art surgical strategy is known to effectively avoid undue damage to long-distance axonal connections in the central nervous system.

Minimally invasive neurosurgical procedures require geometrically accurate, patient-registered, imaging data to facilitate tissue differentiation and targeting. Thus far, true integration of imaging (pre-surgical and intra-operative), surgical access, and resection devices has not been accomplished in the related art. Medical devices remain separately operated; and the surgeon is required to cognitively integrate the information, which, of course, maintains a risk of human error.

Pre-operative imaging data such as Magnetic Resonance Imaging (MRI), Computerized Tomography (CT) and Positron Emission Tomography (PET), is integrated into the surgical room statically through a viewing station, or dynamically through a navigation system. The navigation system registers devices to a patient, and a patient to the pre-operative scans, allowing for instruments to be viewed on a monitor in the context of the pre-operative information.

Intra-operative imaging systems primarily involve microscopes, endoscopes, or external video scopes. These are optical instruments that acquire, record, and display optical wavelength imaging (2D, or stereoscopic) at an increased resolution compared to what can be seen with the surgeon's unassisted eye. This optical information is typically displayed on a screen for the surgeon to view as a video feed, while the navigated MRI/CT/PET data would be presented on a separate screen. Some attempts have been made to offer a small window on the navigation screen to show the optical video, or, likewise, to show overlays from the navigation screen on the optical video. Accurate registration between the modalities, effective interface between the surgeon and the devices, and true integration of the devices remains elusive in the related art.

Port-based surgery is a minimally invasive surgical technique where a port is introduced to access a surgical region of interest using surgical tools. Unlike other minimally invasive techniques, such as laparoscopic techniques, a port diameter is larger than a tool diameter. Hence, the tissue region of interest is visible through the port, wherein exposed tissue in a region of interest, at a depth few centimeters below the skin surface, is accessible through a narrow corridor in the port.

Several related art problems generally preclude or impair the ability to perform port-based navigation in an intra-operative setting. For example, the position of the port axis relative to a typical tracking device (TD) is a free and uncontrolled parameter that prohibits the determination of access port orientation. Further, the limited access which is available, due to the required equipment for the procedure, causes indirect access port tracking to be impractical and unfeasible. Also, the requirement for angulation of the access port to access many areas within the brain during a procedure makes navigation of the access port a difficult and challenging problem that has not yet been addressed.

Further, a recent paper by Stieglitz et al., "The Silent Loss of Neuronavigation Accuracy: A Systematic Retrospective Analysis of Factors Influencing the Mismatch of Frameless Stereotactic Systems in Cranial Neurosurgery," highlights the need for accurate navigation, wherein after patient registration, an ongoing loss of neuronavigation accuracy remains due to other mitigating factors related to the surgical procedure, i.e., draping, attachment of skin retractors, and duration of surgery. Surgeons should be aware of this "silent" loss of accuracy when using related art navigation systems.

Accordingly, challenges experienced in the related art include an inability to perform a real-time registration of a surgical trajectory in relation to the unique characteristics of a particular tissue types or sub-types, such as in relation to cerebral tissue. Therefore, a need exists for a system and method that integrates and updates pre-operative and intra-operative plans into navigation systems for minimally invasive surgical procedures, such as an improved system and method for mapping navigation space to patient space in a medical procedure, e.g., as a real-time registration of a surgical trajectory in relation to the unique characteristics of a particular tissue types or sub-types, for example, cerebral tissue.

SUMMARY

The invention described herein provides a method of optical coherence tomography (OCT) image acquisition, using a computer processor, an OCT imaging system, a three dimensional imaging system and a navigation system, to provide a multi-scale three dimensional visual representation of a patient intraoperatively. The patient has a surface and has discernable surface and subsurface features. The method includes multiple steps as follows. A three dimensional imaging scan of a portion of the surface of the patient using the three dimensional imaging system is acquired. A three dimensional imaging system can be, but not limited to, a structured light camera, stereoscopic camera involving photometric imaging and geometric imaging and ultrasound transducer. The three dimensional imaging scan of the portion of the patient is registered with the patient intraoperatively. A first OCT imaging scan covering a first sub-portion of the portion of the patient using the OCT imaging system is acquired. The OCT imaging system is tracked by the navigation system. A second OCT imaging scan covering a second sub-portion of the portion of the patient using the OCT imaging system is acquired. The first OCT imaging scan and the second OCT imaging scan are stitched together using a stitching algorithm to produce an amalgamated OCT image. The three dimensional imaging scan and the amalgamated OCT image are combined to create an enhanced three dimensional image of the portion of the patient. This is then repeated to capture a very wide high resolution OCT image that is registered and overlaid with another three dimensional image in an enhanced multi-scale three dimensional image of the patient.

The combining of the three dimensional imaging scan and the amalgamated OCT image may include forming a spatial correspondence between the amalgamated OCT image and the registered three dimensional image of the patient.

The method may also include a step of displaying the enhanced three dimensional image.

The stitching of the OCT imaging scans may include the computer processor correlating overlapping portions of the OCT imaging scans to identify common features in the two OCT imaging scans. The common features may include one or more subsurface features.

The combining of the three dimensional imaging scan and the amalgamated OCT image may be done so that pixels in the three dimensional imaging scan that correspond to locations in the sub-portions covered by the amalgamated OCT image are replaced by values derived from the amalgamated OCT image. The three dimensional imaging system may also be tracked by the navigation system. The three dimensional imaging system may employs structured light. The OCT imaging scans may be formed from a plurality of B-scans. The invention described herein provides an image acquisition system for providing a three dimensional visual representation of a patient intraoperatively. The patient has a surface having discernable surface and subsurface features. The system includes an OCT imaging system, a three dimensional imaging system, a navigation system and a computer processor configured to perform a number of functions as follows. The computer processor is configured to acquire a three dimensional imaging scan of a portion of the surface of the patient using the three dimensional imaging system. The computer processor is further configured to register the three dimensional imaging scan of the portion of the patient with the patient intraoperatively. The computer processor is further configured to acquire a first OCT imaging scan covering a first sub-portion of the portion of the patient using the OCT imaging system, wherein the OCT imaging system is tracked by the navigation system. The computer processor is further configured to acquire a second OCT imaging scan covering a second sub-portion of the portion of the patient using the OCT imaging system. The computer processor is further configured to stitch together the first OCT imaging scan and the second OCT imaging scan using a stitching algorithm to produce an amalgamated OCT image. The computer processor is further configured to combine the three dimensional imaging scan and the amalgamated OCT image to create an enhanced three dimensional image of the portion of the patient. The computer processor is further configured to display the enhanced three dimensional image.

In such systems, the combining of the three dimensional imaging scan and the amalgamated OCT image may include forming a spatial correspondence between the amalgamated OCT image and the registered three dimensional image of the patient. The stitching of the OCT imaging scans may include the computer processor correlating overlapping portions of the OCT imaging scans to identify common features in the two OCT imaging scans. The common features in the OCT imaging scans may include one or more subsurface features. The combining of the three dimensional imaging scan and the amalgamated OCT image may be done so that pixels in the three dimensional imaging scan that correspond to locations in the sub-portions covered by the amalgamated OCT image are replaced by values derived from the amalgamated OCT image. The three dimensional imaging system may also tracked by the navigation system. The three dimensional imaging system may employ structured light. The OCT imaging scans may be formed from a plurality of B-scans.

BRIEF DESCRIPTION OF THE DRAWINGS

Embodiments will now be described, by way of example only, with reference to the drawings, in which.

DETAILED DESCRIPTION

Figure 1:
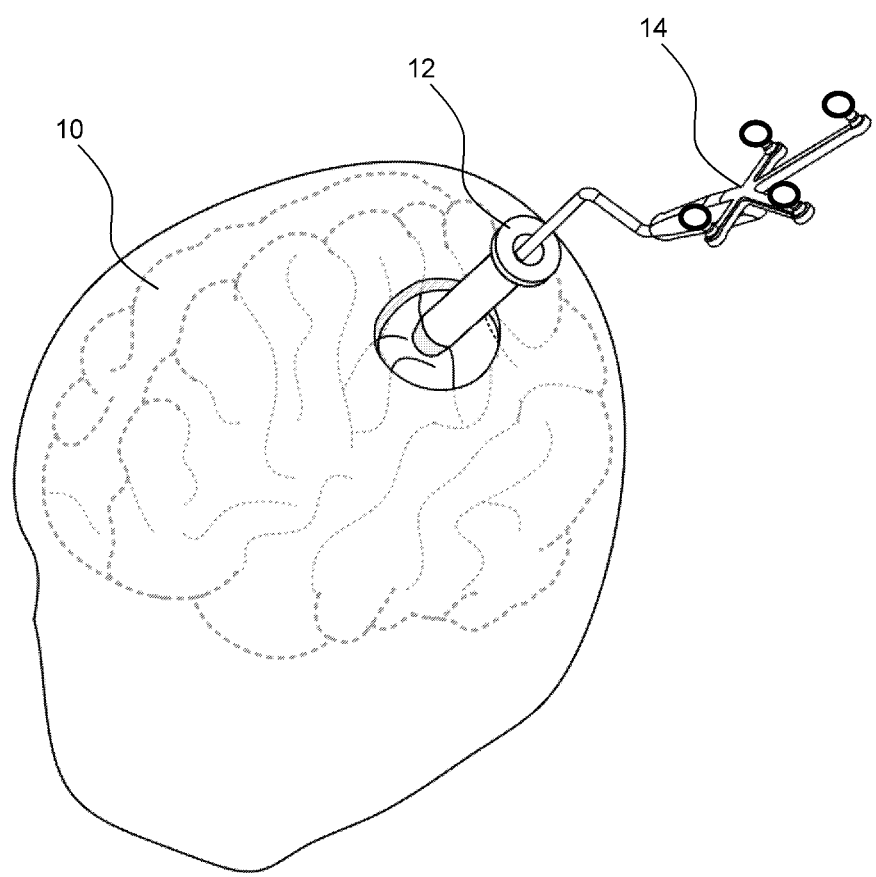
FIG. 1 illustrates the insertion of an access conduit into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Some embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

In some embodiments, a 3D scanner, such as an optical scanner using structured light, is used to acquire a 3D scan of the patient being operated on. The 3D scan produces a 3D image of a portion of the surface of the patient, in combination with a high resolution imaging system. The "surface" of the patient is intended to mean all portions of the patient's body that would, at a given point during an operation, reflect light transmitted by a device towards the patient. For example, the surface includes any internal portions of the patient's brain that have been exposed during the operation, including any portions visible via an access port. The 3D scanner provides three dimensional images, each comprising a two dimensional array of pixels, representing the reflectance of the corresponding points on the surface of the patient, as well as depth information that may be incorporated into the images as contour lines.

The present disclosure is generally related to medical procedures, neurosurgery, and minimally invasive surgery to be specific.

In the example of a port-based surgery, a surgeon or robotic surgical system may perform a surgical procedure involving tumor resection in which the residual tumor remaining after is minimized, while also minimizing the trauma to the healthy white and grey matter of the brain. A beneficial input that may assist minimization of residual tumor and healthy tissue damage may be visualization of the area of interest using high resolution OCT imaging providing a greater capacity to resolve the unhealthy brain tissues.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments 14 may then be inserted down the access port 12.

Optical tracking systems, which may be used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked. It should be noted that any embodiments provided herein using which employ an optical tracking system may be extended to any relevant tracking system as are known in the art, and thus the examples provided below should not be taken to limit the scope of the invention as disclosed herein.

Figure 2:
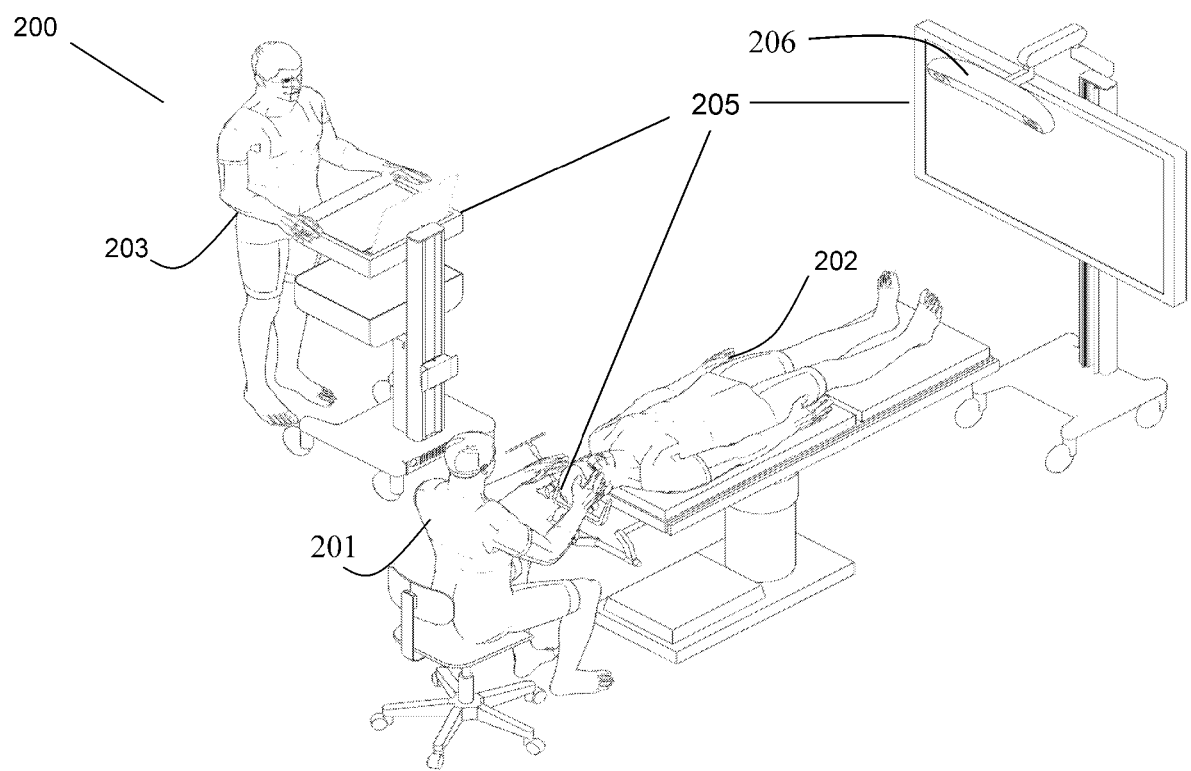
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system 206, displays and tracked instruments assist the surgeon 201 during his procedure. An operator 203 is also present to operate, control and provide assistance for the medical navigation system 205. A detailed description of a surgical navigation system is outlined in international application PCT/CA2014/050270, entitled "SYSTEMS AND METHODS FOR NAVIGATION AND SIMULATION OF MINIMALLY INVASIVE THERAPY", which claims priority to U.S. Provisional Patent Application Ser. Nos. 61/800,155 and 61/924,993, which are all hereby incorporated by reference in their entirety.

Figure 3:
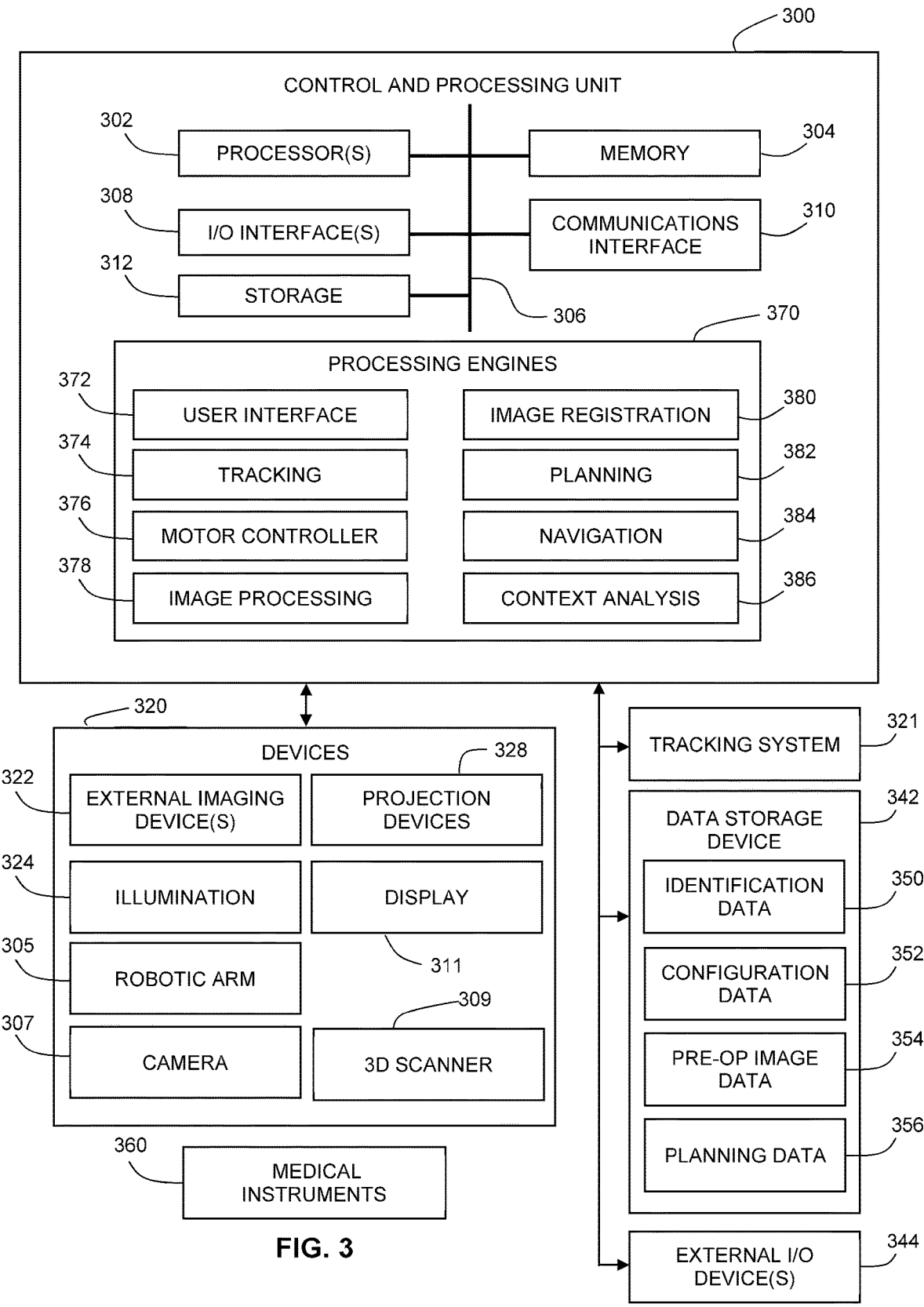
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, a sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, an automated arm 305, one or more projection devices 328, one or more 3D scanning devices 309, (such as CT, MRI, structured light and etc.) and one or more displays 311. Examples of external imaging devices 322 include OCT imaging devices and ultrasound imaging devices.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using magnetic tracking instead of infrared cameras, and or active tracking markers.

Figure 4:
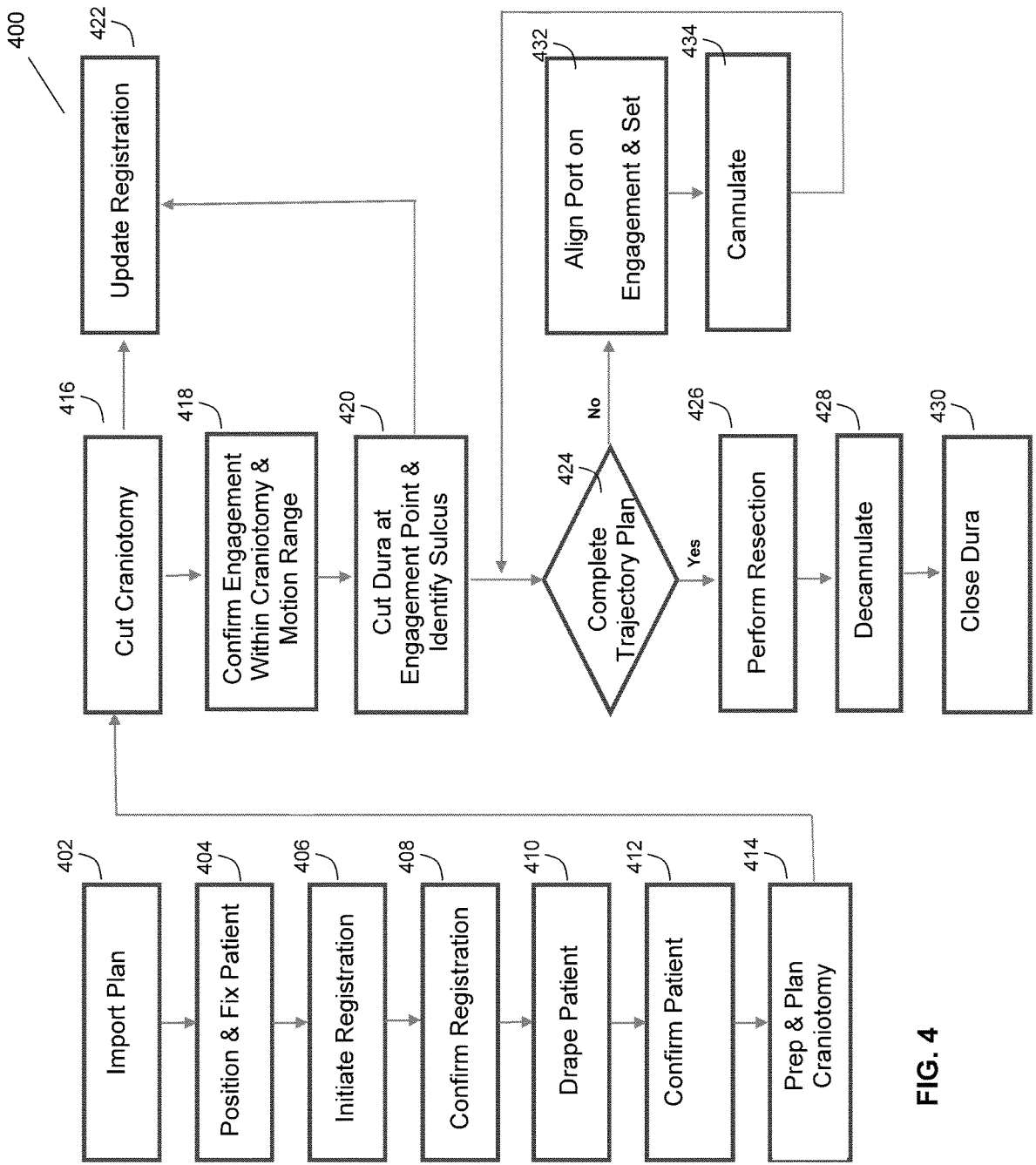
FIG. 4 is a flow chart illustrating a method involved in a surgical procedure using the navigation system of FIG. 2.

Referring to FIG. 4, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by the computer or controller forming part of the equipment tower 201.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. "Registration" is also used in the present application to map a preoperative image of a patient to that patient in a physical tracking space.

Those skilled in the relevant arts will appreciate that there are numerous image registration techniques available and one or more of the techniques may be applied to the present example. Non-limiting examples include intensity-based methods that compare intensity patterns in images via correlation metrics, while feature-based methods find correspondence between image features such as points, lines, and contours (both in plane or 3D). Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include image registration of brain computerized tomography (CT)/MRI images or PET/CT images for tumor localization, registration of contrast-enhanced CT images against non-contrast-enhanced CT images, and registration of ultrasound and CT to patient in physical space.

Figure 5:
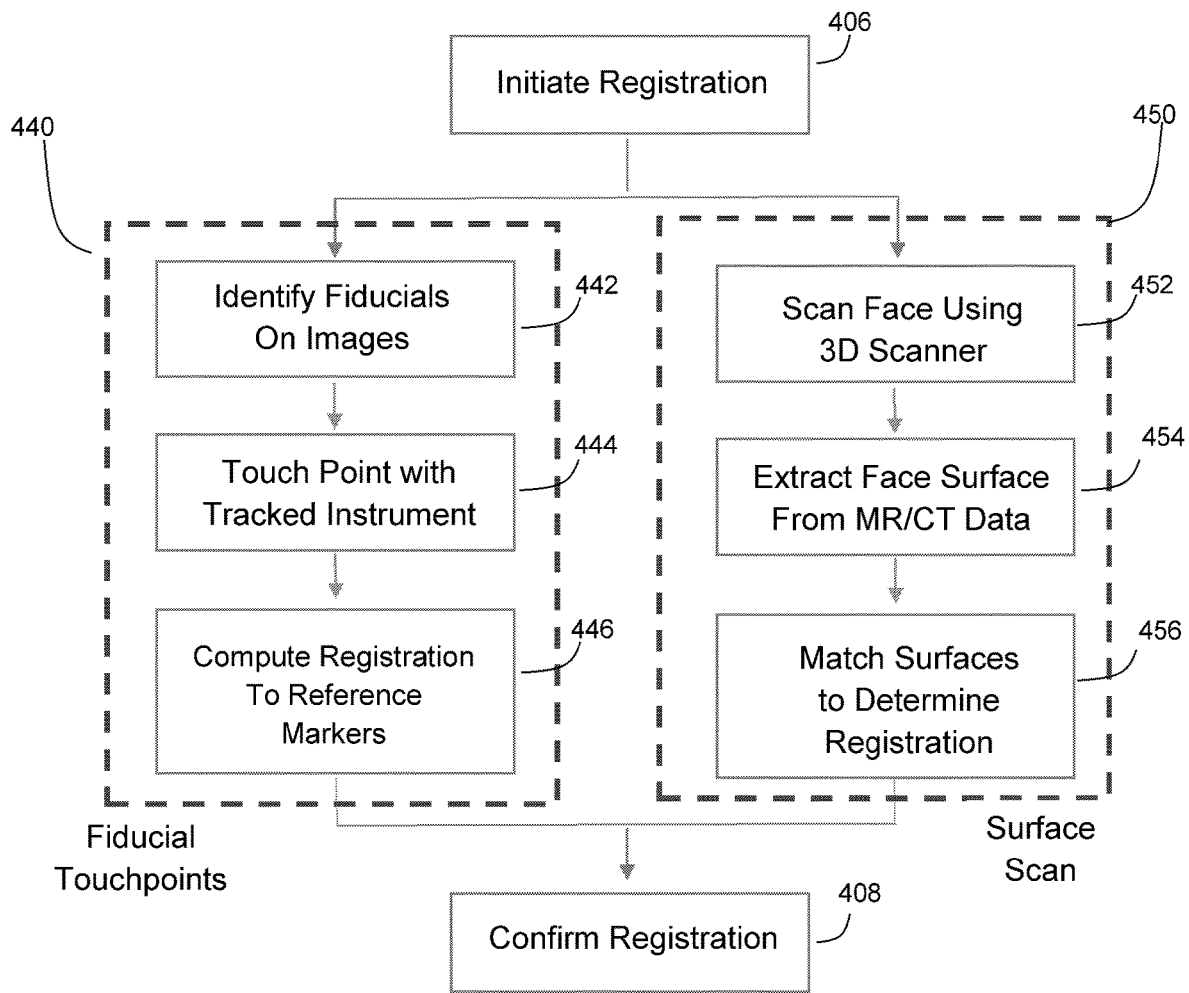
FIG. 5 is a flow chart illustrating a method of registering a patient for a surgical procedure as outlined in FIG. 4.

Referring now to FIG. 5, a flow chart is shown illustrating a method involved in registration block 406 as outlined in FIG. 4 in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4.

Referring back to FIG. 4, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). In some procedures registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs a resection or the like (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4 are specific to port-based surgery, such as portions of blocks 428, 420, and 434, but the appropriate portions of these blocks may be skipped or suitably modified when performing non-port based surgery.

Figure 6:
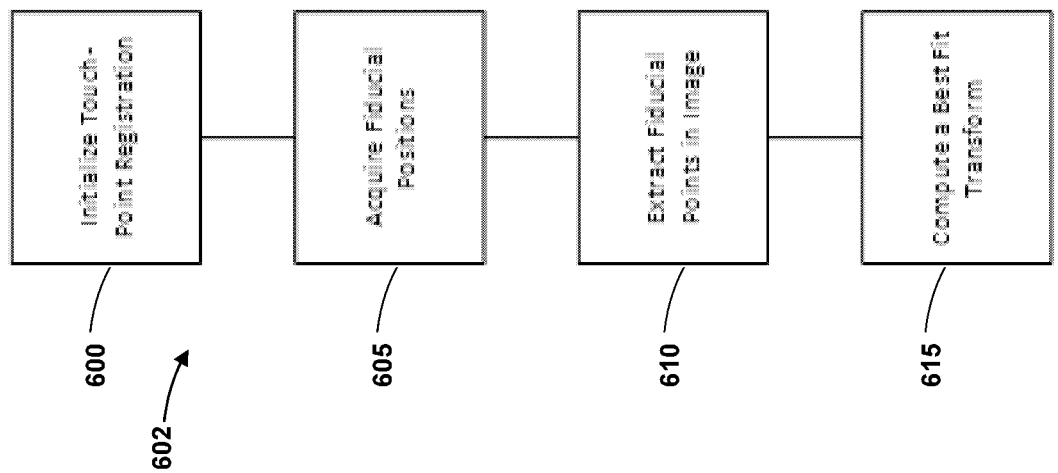
FIG. 6 is a flow chart illustrating a method of registering a patient for a medical procedure with a medical navigation system using a patient reference device.
Figure 6:
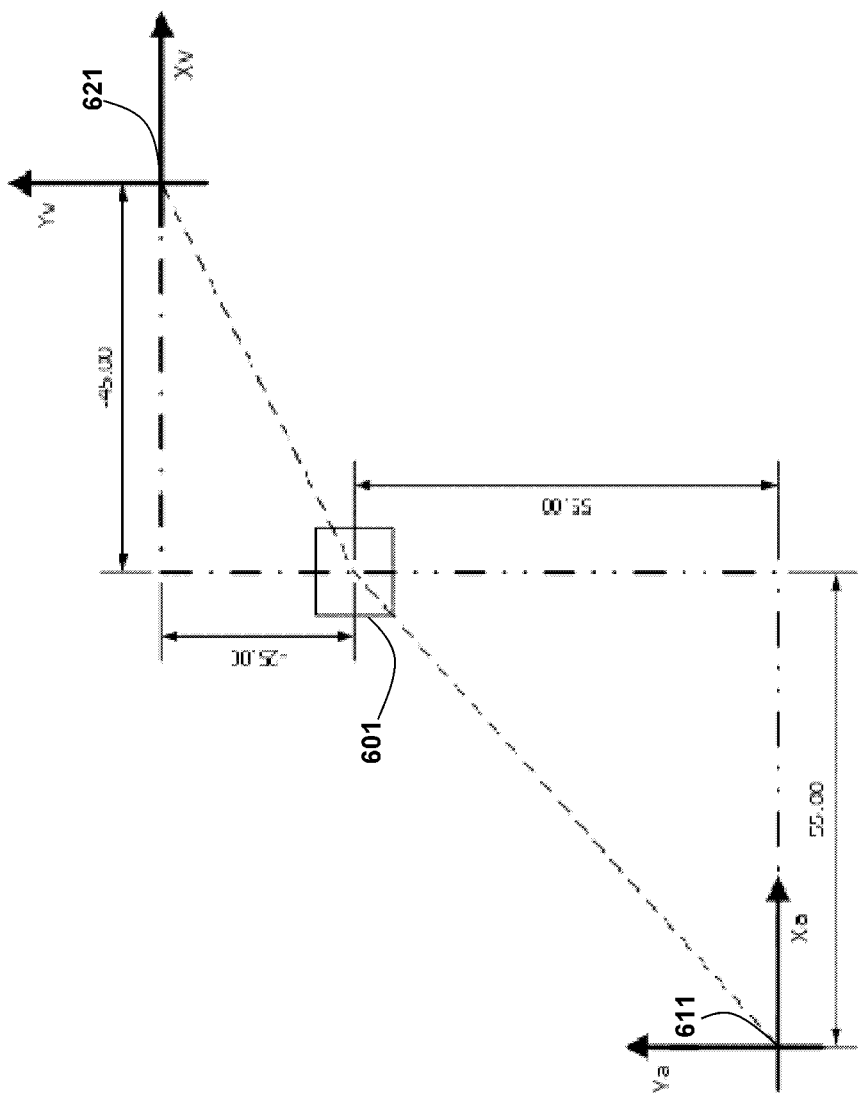

Referring now to FIG. 6, a registration process, similar to that which may be used in block 450 of FIG. 5, is shown for computing a transform that may be used to import coordinates from the physical coordinate space of the operating room to the image space of the MRI image. Resultantly any tool positions in the physical coordinate space may be registered to the image space via the application of this transform.

In order to derive this transform for importing objects from a physical coordinate space to an image space, the two spaces must be coupled with a "common reference", having a defined position that can be located in both the physical and image coordinate spaces. The process of patient registration for surgical navigation uses identifiable points located on a patient anatomy visible both on the patient and on the patients scan as the common reference point(s). An example of a common reference is shown in FIG. 6 as 601 along with the physical and image coordinate space origins, 611 and 621 respectively. It is apparent from the figure that the common references position is known in both spaces. Using these positions a transform may be derived that facilitates the importation of the position of any point in the physical coordinate space into the image space. One way to determine the transform is by equating the locations of the common reference in both spaces and solving for an unknown translation variable for each degree of freedom defined in the two coordinate spaces. These translation variables may then be used to convert a set of coordinates from one space to the other. An exemplary transform may be derived as per the diagram shown in FIG. 6. In the figure the position of the common reference 601 is known relative to the physical coordinate space origin 611 and the image space origin 621. The common references position may be extracted from the diagram as follows:

$(Xcra, Ycra) = (55, 55)$ and $(Xcrv, Ycrv) = (-45, -25)$

Where the subscript "cra" denotes the common reference position relative to the physical coordinate space origin and the subscript "crv" denotes the common reference position relative to the image space origin. Utilizing a generic translation equation describing any points ((Ya, Xa) and (Yv, Xv)), where the subscript "a" denotes the coordinates of a point relative to the physical coordinate space origin 611, and the subscript "v" denotes the coordinates of a point relative to the image space origin 621, we can equate the individual coordinate elements from each space to solve for translation variables ((YT, XT)), where the subscript "T" denotes the translation variable as shown below.

$Yv = Ya + YT$ $Xv = Xa + XT$

Now substituting the derived values of the points from FIG. 6 we can solve for the translation variable.

$-45 = 55 + YT$ $YT$

And $-25 = 55 + XT$ $80 = XT$

Utilizing these translation variables, any position (i.e. (Ya, Xa)) defined relative to the common reference in the physical coordinate space may be transformed into an equivalent position defined relative to the common reference in the image space through the two generic transformation equations provided below. It should be noted that these equations may be rearranged to transform any coordinates of a position from the image space into equivalent coordinates of a position in the physical coordinate space as well.

$Xa = Xv + 100$ and $Ya = Yv + 80$

The resulting transform thus enables the position of any object to be transformed from the physical coordinate space to the image space. Thus the two spaces become coupled with the transform enabling the registration of objects from the physical space to the image space. It should be noted that in practice the common reference is usually a set of points (as opposed to a single point) from the patients anatomy that may be located both on the anatomy of the patient in the physical coordinate space of the operating room and in the image of the patient. Using a set of points may be more advantages than a single point as it further restricts degrees of freedom and thus more accurately defines an objects position in space. More specifically in a spatial coordinate system such as the physical coordinate space of the operating room an object may have six degrees of freedom, three spatial degrees of freedom most commonly referred to as (x, y, z) and three rotational degrees most commonly referred to as (pitch, yaw, roll) that may be used to define the object position entirely. Accordingly one manner to transfer these degrees of freedom upon transformation from the physical coordinate space to the image space is to apply the transform to three or more points on the object.

Figure 7:
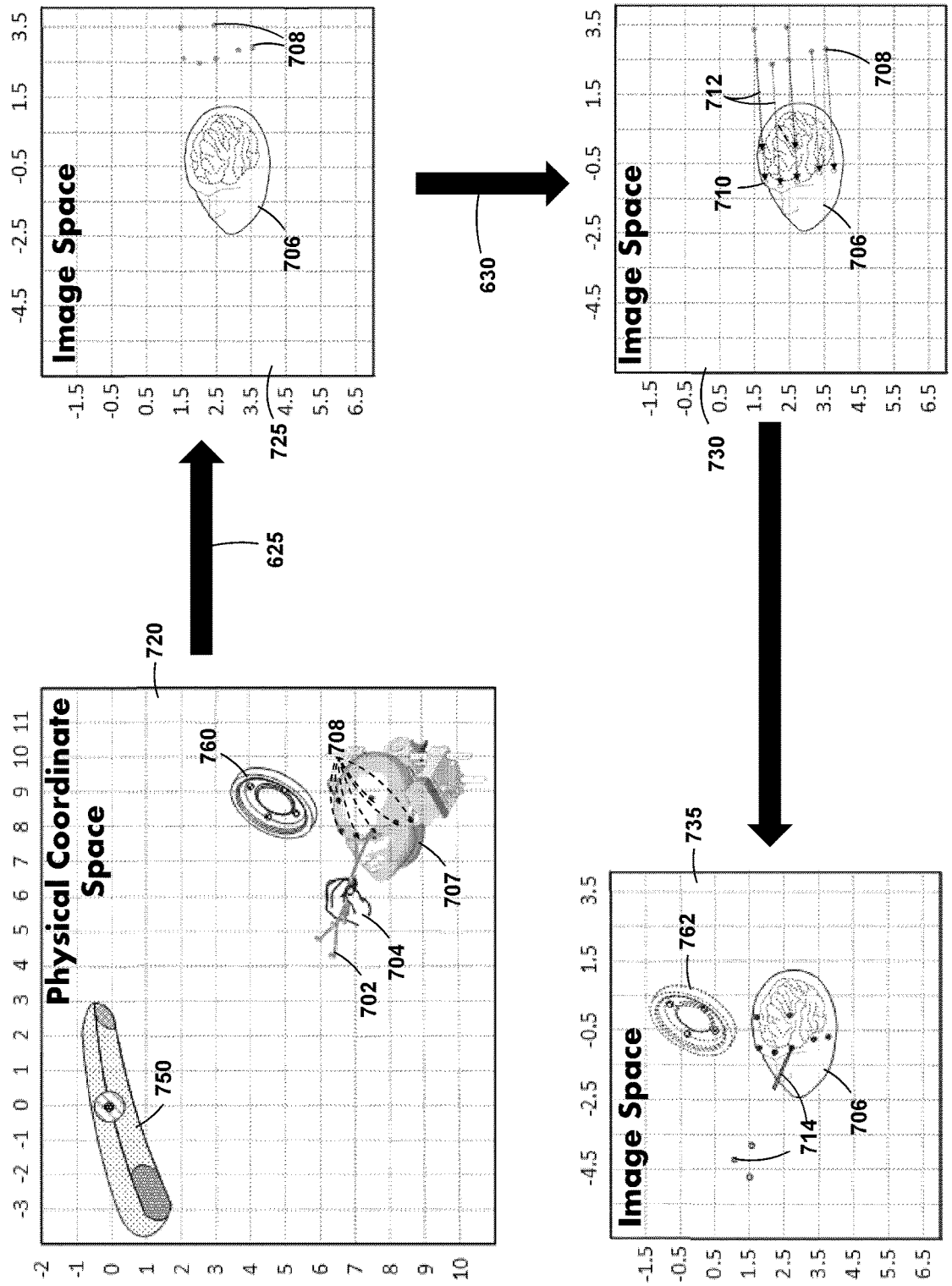
FIG. 7 is diagram illustrating the process of patient registration.

To further elaborate on the process of registration a practical implementation will be described in further detail as follows. A flow chart describing the practical method of performing a patient registration is provided in FIG. 6. The registration method 602 describes a touch-point registration method. FIG. 7 shows an illustrative diagram of each step in performing a registration using the touch-point method 602. In an embodiment these methods may be executed via the use of a navigation system such as shown in FIG. 3 and any steps may be programmed into the navigation system processor 300, stored in memory 304, and called upon by the navigation system as required.

The first step in this method 600 is to initialize the touch-point acquisition process. During this step a user may prompt the navigation system processor such as processor 302 in FIG. 3 to initiate said touch-point acquisition process. To clarify, a touchpoint acquisition process may refer to the priming of the system to acquire a pointer position upon determining the pointer to be at the position of a fiducial point. In an alternate embodiment the system itself may initiate a touch-point registration process without the input of the user, such as upon the system workflow advancing to the touch-point registration mode, or upon the detection of specific trackable medical instruments such as by tracking system 321.

Once the touch-point registration process is initiated 600 the following step is to acquire one or more fiducial positions 605 in the physical coordinate space of the operating room. FIG. 7 depicts an illustration of this step as 625. As is shown in the figure a user 704 is identifying fiducials 708 on a patient 706 using a tracked pointer tool 702. The tracking camera 750, connected to the surgical navigation system, collects the positions of the fiducial points 708 via the tracked pointer tool 702 and passes them to the navigation system processor which either stores the points in the image space containing the patient image, such as the points 708 in the image space 725, or alternatively in memory. In some cases the tracking system is constantly tracking the pointer tools position thus in order to record the position of the pointer tool at the correct time (i.e. when it is placed on a fiducial), the system maybe prompted by the user. This prompt may be facilitated through the use of a switch type device such as a foot pedal or mouse that are connected to the surgical navigation system.

Once the fiducial points are acquired 605 the following step is to extract the scanned fiducial points from the patient image 610. FIG. 7 depicts an illustration of this step 630. As is shown in the figure the scanned fiducials 710 are segregated from the rest of the patient image 706 in the image space 730. In some cases the segregation of the fiducials from the image of the patient may be completed manually by a user. Where the user indicates the fiducial positions on the patient image to the surgical navigation system through a graphical user interface. While in other cases the surgical navigation system may be programmed with instructions to segregate the positions of the scanned fiducials from the patient image automatically. Thus step 610 may be performed by either a user or a surgical navigation system.

Figure 8:
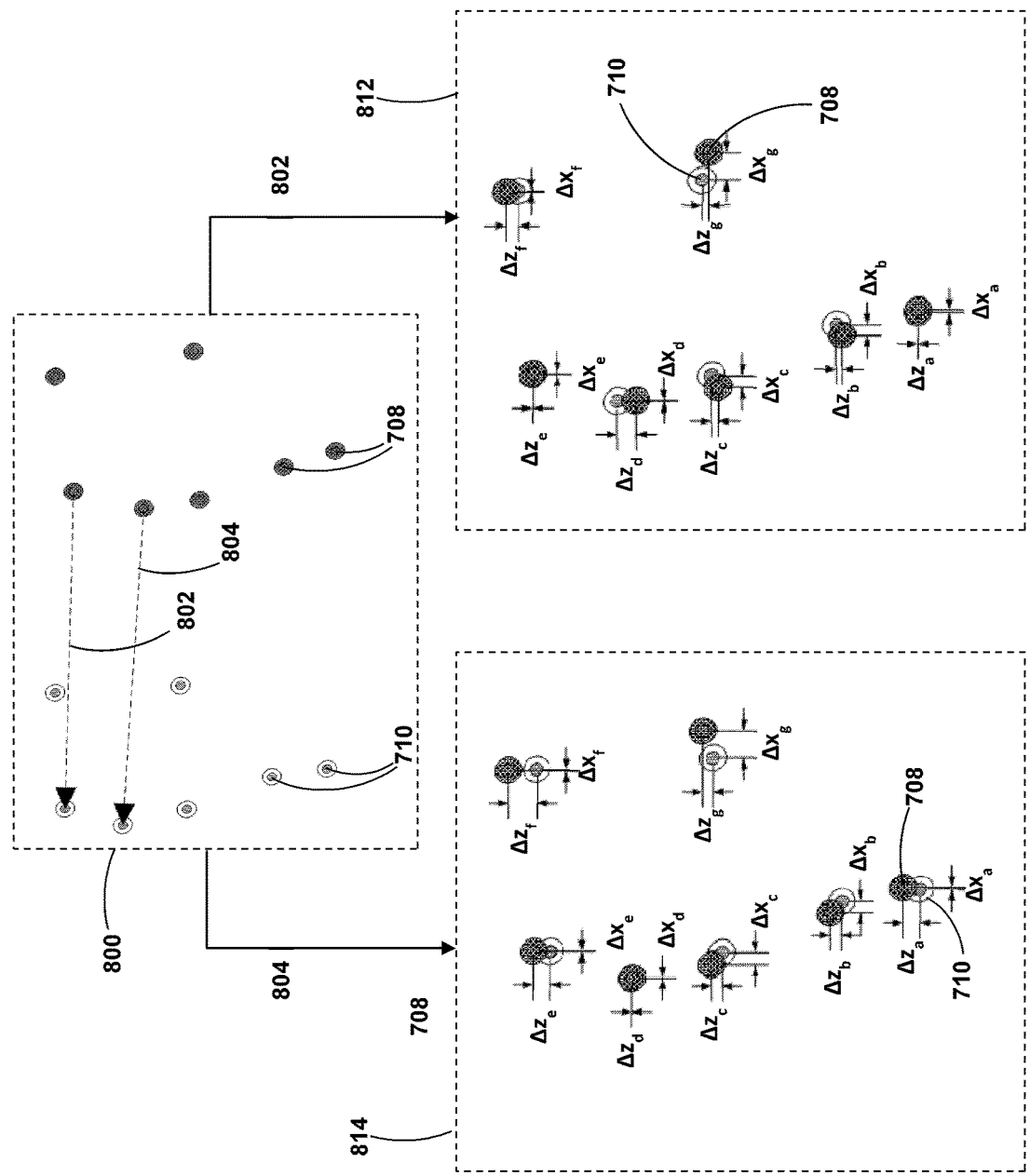
FIG. 8 is a diagram illustrating the process of deriving a patient registration transform.

Once the scanned fiducial points are extracted from the patient image 610 the following step is to compute a best fit transform 615. FIG. 7 depicts an illustration of a computed transform 712 as per the example provided. It is apparent from the figure that the transform 712 is computed such that the fiducial points 708 acquired from the physical coordinate space align with the extracted fiducials 710. In general the completion of this step 615 requires the navigation system processor to compute a single transform that when applied to each fiducial point 708 in the image space individually, will align them with their scanned fiducial counterparts 710. However given practical limitations of technology perfect alignment is problematic to achieve for all of the fiducial points using a single transform. Thus to approximate a perfect alignment the processor instead derives a transform that minimizes the deviation in alignment between the extracted fiducials from the patient image and the fiducial points on the patient. For example as shown in FIG. 8 the transforms 802 and 804 both attempt to align the fiducial points 708 with their counterparts 710 in the image space 800. Such transforms may be derived by iteratively applying a cost minimization function to the initial set of fiducial points with arguments being the sum of spatial deviances $\Delta x_{a \to g}$ and $\Delta z_{a \to g}$ between the two sets of points 708 and 710. In one example, the iterative cost minimization function may take the form of an Iterative Closest Point (ICP) approach to calculate the registration transformation, such as that detailed in "A Method for Registration of 3-D Shapes" by Paul J. Besl and Neil D. McKay, IEEE Transactions on Pattern Analysis and Machine Intelligence, pp. 239-256, VOL. 14, No. 2, February 1992, the entirety of which is hereby incorporated by reference. However, any suitable approach may be used depending on the design criteria of a particular application. For example as shown in FIG. 8 the iterative computation may in one iteration produce the transform 804 that when applied to the fiducial points 708 produces the alignment of points shown in frame 814 of FIG. 8. While in a subsequent iteration may produce the transform 804 that when applied to the fiducial points 708 produces the alignment of points shown in frame 812 of FIG. 8. The processor may then execute the cost minimization function to compare the sum of the deviances $\Delta x_{a \to g}$ and $\Delta z_{a \to g}$ for each result 814 and 812 and select the one with the lowest value for the next iteration and so on until the deviation value falls below a certain threshold value or meets some alternately defined criteria. It is apparent from the case shown in FIG. 8 that the transform which minimizes the spatial deviances $\Delta x_{a \to g}$ and $\Delta z_{a \to g}$ when applied to the fiducial points 708 is the transform 812.

Referring back to FIG. 6, once step 615 is completed and a transform is derived it may then be used to transform any points from the physical coordinate space of the operating room into the image space, effectively coupling the two spaces. Referring back to FIG. 7 this aspect of the patient registration process is illustrated by the physical coordinate space 720 and the image space 735 where the spatial alignments between the patient 707, the patient reference 760, and the pointer tool 702 is duplicated by the virtual representations of these objects in the image space 720. i.e. by the patient scan 706, the virtual patient reference 762 and the virtual pointer tool 714 in the image space 735.

Figure 9:
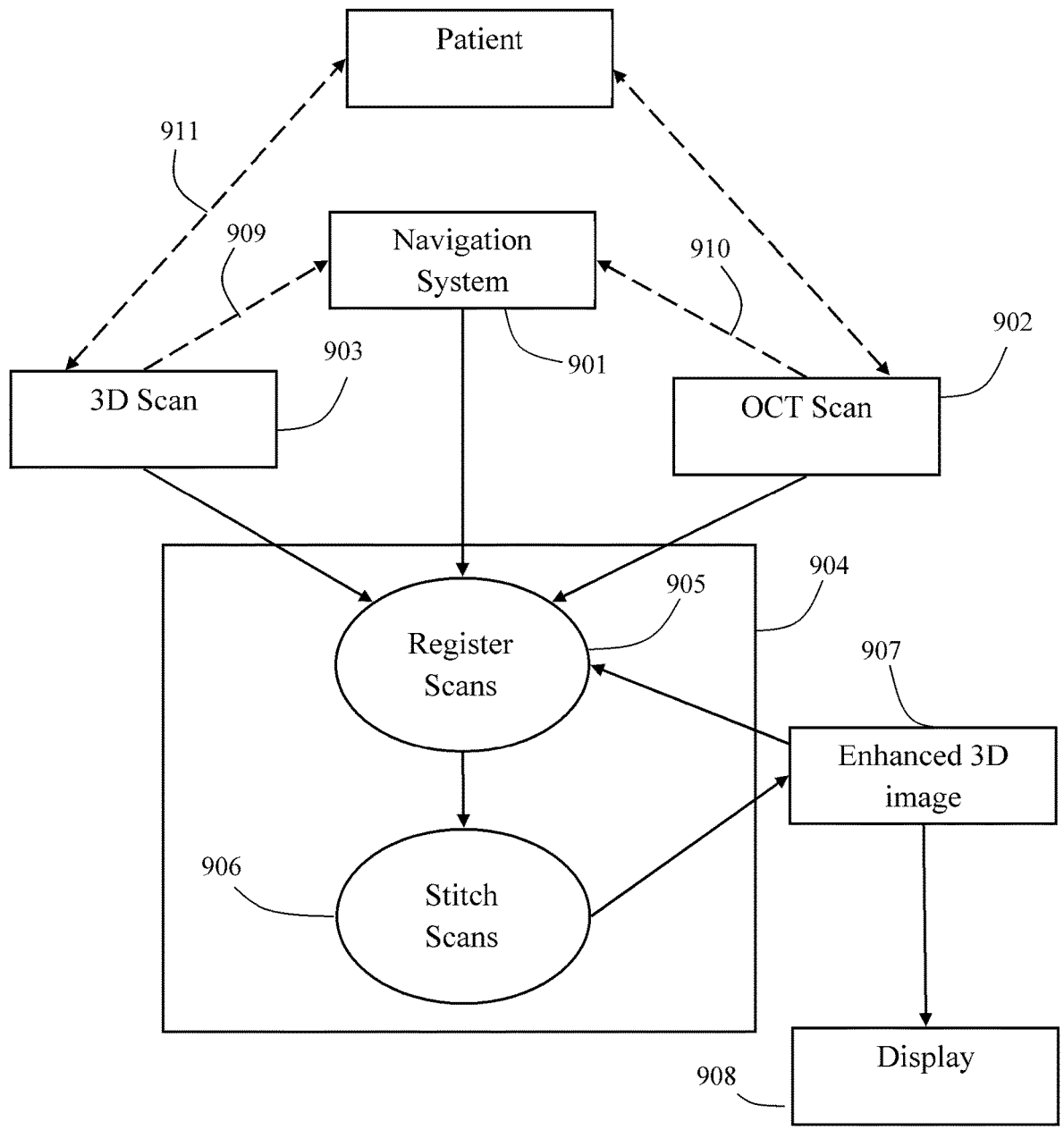
FIG. 9 is a flow chart showing an embodiment of implementing the system as disclosed herein.

Referring now to FIG. 9 an illustrative diagram of an embodiment of the invention described herein is provided. The system depicted is formed of many interdependent parts. Each of which will be elaborated on further as follows.

The 3D scan 903 shown in FIG. 9 may be any acquired scan of an anatomy of the patient having a surface and potentially subsurface features. In some embodiments these scans may be specific to the brain containing brain structures such as nerve fibers (white matter), ventricles, sulci, gyri, or the like, while in other embodiments these may take the form of alternate anatomical regions of the body containing anatomical structures such as muscle fibers, bone, prostate, and etc. The term 3D scan as used herein includes any imaging of the patient that may be used to reconstruct a 3D visualization of the patient. Some non-limiting examples of such visualizations include CT scans, MRI scans, structured light imaging, OCT imaging, and the like. In addition these examples also include any combination thereof.

In some embodiments these 3D scans may be registered to the patient anatomy such as by the fiducial-point, surface trace, and structured light patient registration methods described above. Thus facilitating the mapping of objects from the physical tracking space of the operating theater to the image space containing the 3D scan.

The OCT scan 902 shown in FIG. 9 is acquired using OCT imaging. To provide some background OCT imaging is an imaging modality that may be used to produce a high resolution image of a sub-portion of the patient anatomy. In certain applications OCT imaging may provide a surgeon with some added benefits as is known in the art. Such benefits may include providing them access to high resolution imaging of a patient's anatomy, allowing for subsurface tissue visualization, providing the ability to operate in small openings and corridors when mounted on a probe, the ability to acquire imaging with non-contact tissue interrogation, and the ability to be utilized intraoperatively. Optical coherence tomography is based on low-coherence interferometry, typically employing near-infrared light. The use of relatively long wavelength light allows it to penetrate through the surface of the patient and so obtain reflections from internal features under the interrogated patient surface. To the extent the light penetrates the surface, all points under the surface will reflect some energy, but some subsurface portions, such as those containing changes in properties relative to their surroundings, will reflect varying amounts and allow high-resolution 3D imaging of the associated internal structure. For example, natural barriers such as fat layers and tumor margins as well as density changes among internal tissues will tend to reflect a substantially different amount of light in comparison to the surrounding matter, allowing the system to detect these changes. Functional OCT further provides imaging of micro-vasculature and polarization contrast showing tissue organization which are extremely useful for surgeons during a procedure when these images are provided in different resolution scale and field-of-view in particular with a wide field high resolution image.

Figure 10:
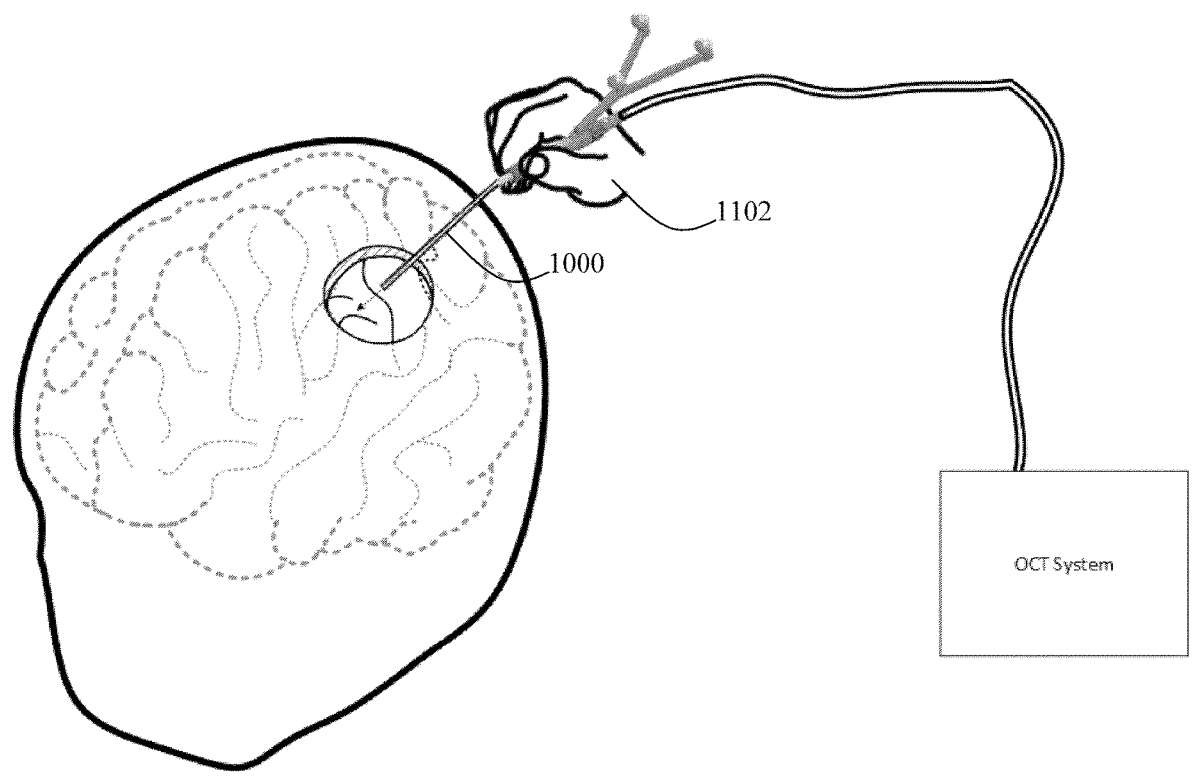
FIG. 10 is a diagram depicting the use of an embodiment of the system as disclosed herein.
Figure 11:
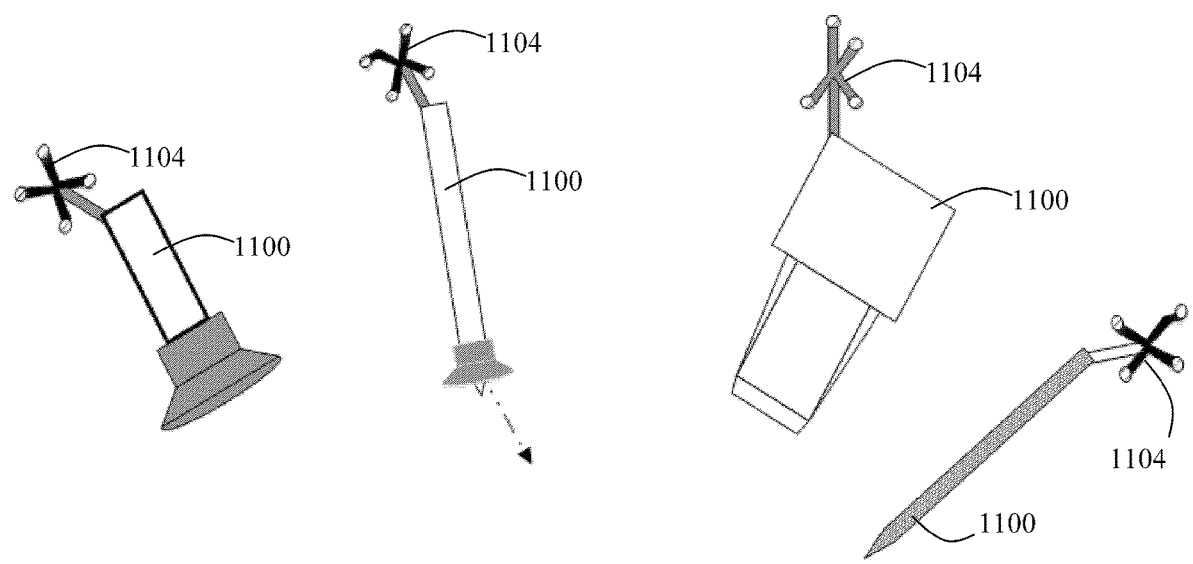
FIG. 11 is a diagram depicting different instances of OCT probes.

In some embodiments the OCT imaging system may include a trackable probe portion such as probe portion 1000 depicted in FIG. 10 that may incorporate an optical transmitter and receiver for interrogating tissue, and may be positionable by an operator 1102 such that it may be maneuvered during a surgical procedure as the operation progresses. As shown in FIG. 9 in a preferred embodiment the position of the OCT scan may be computed continuously 910 via a tracking component of the navigation system 901 in the same way that tools are tracked by the tracking system component of the navigation system 901 as described above. The tracking of the probe may be enabled in some embodiments by mounting it with a tracking tree 1104 such as those depicted on the OCT probe portions 1100 shown in FIG. 11. In alternate embodiments the position of the probe in the physical coordinate space of the operating theater may be recorded as well as imported into the image space containing the 3D scan. By way of image processing the OCT scan may be interrogated to determine the distance of the surface of an OCT scan from the probe that was used to acquire it. This information may subsequently be used to register the acquired OCT scan with the image space containing the 3D scan as is described in more detail as follows.

While the OCT probe provides a high resolution surface image, it may also produce true three dimensional subsurface imaging (or a "volume scan"). For each point on the surface of the patient imaged by the OCT probe for example, a time series of values in the form of an optical signal is obtained (being an "A-scan"), each value associated with a particular time corresponding to the distance of the probe to the internal structure that produced the particular pixel value (i.e. the echo of the optical light from the different layers of the internal structure). These distance values may later be used to reconstruct an A-scan OCT image in an OCT image space. In frequency domain OCT, the time series of values is obtained though acquiring the power spectrum (i.e. the power of the signal reflection from the internal structure at different frequencies) and performing a Fourier-transform on the power spectrum. The surface will always be the first significant reflection, which often will also be the largest value in the A-scan. A B-scan may be obtained by taking a series of A-scans along a line and combining them. In turn, multiple B-scans can then be taken and combined to image a full 3D volume OCT image.

Figure 12:
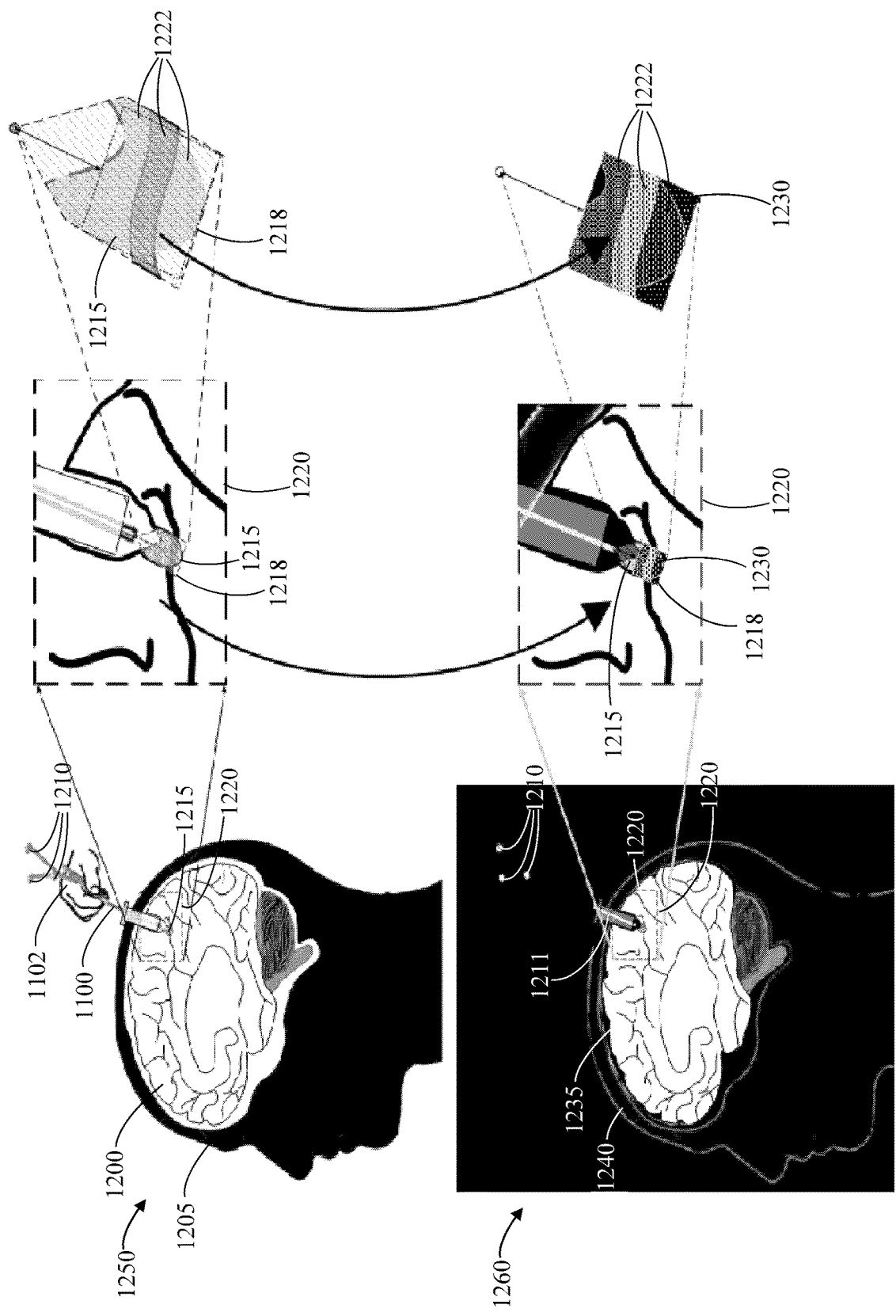
FIG. 12 is a diagram showing the stitching of an OCT image into a 3D image of a patient.

The combination of A-scans into a B-scans and subsequently into a C-scan may be achieved by generating the A-scans in an OCT image space based on their positions relative to the interrogation point of the probe. This is commonly accomplished during acquisition, where the directions of all the acquired A-scans relative to the interrogation point may be recorded. It should be noted that the interrogation point of the probe generally refers to the point from which the optical interrogation signal is emitted and collected. In order to acquire multiple A-scans, the light emanating from the interrogation point may be directionally guided via any directional guidance mechanisms that are known in the art, such as a galvanometer. In order to produce a 3D volume OCT image from the combination of OCT A-scans acquired using the probe, subsequent A-scans may be guided in a scan pattern, such as raster scan, across the surface of the tissue. Resultantly the directional information recorded for each A-scan along with the knowledge that the A-scans were all acquired via the same interrogation point may be used to facilitate the generation of an image from the A-scans in an OCT image space. For example, as shown in FIG. 12, beginning with the cross sectional diagram 1250 of a patient in physical space, a user 1102 performing neurosurgery on a patient 1205 is shown acquiring an internal OCT scan (i.e. a cross-sectional plane of an OCT volume or c-scan) 1230 of the patient's brain 1200 within a surgical area of interest 1215, using an OCT probe 1100. To further elaborate, a region containing the surgical area of interest is magnified in box 1220, and this region is further magnified in box 1218, which shows an exemplary scanning area of a surgical area of interest 1215 containing tissue. After (or in some instances during) the acquisition of an OCT scan of the scanning area 1215, the acquired A-scans may be transformed into an OCT image space to form an OCT image. For example, as shown in the figure the OCT image 1230 derived from the scanning area 1218. As is apparent from this figure the OCT image 1230 of the scanning area 1218 contains the various sub-regions 1222 of the tissue within the surgical area of interest 1215.

Figure 13:
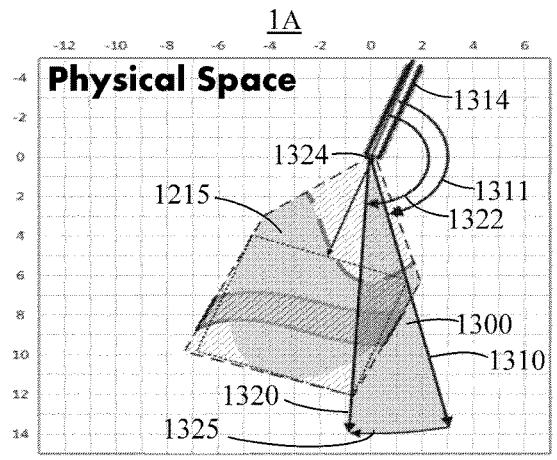
FIG. 13 is a diagram showing the acquisition of an OCT scan and its formation in an OCT image space.
Figure 13:
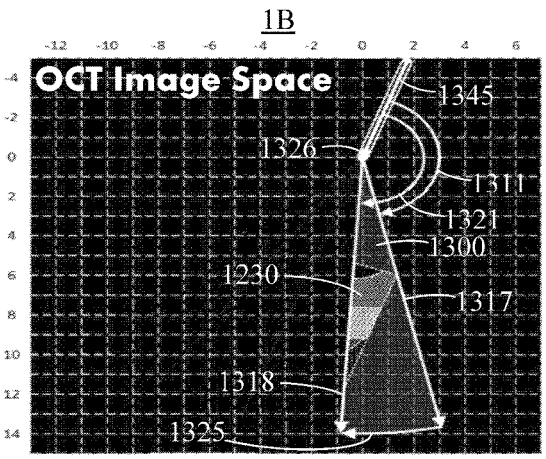
Figure 13:
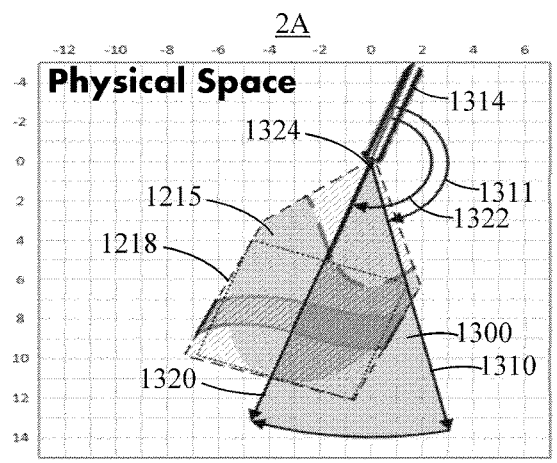
Figure 13:
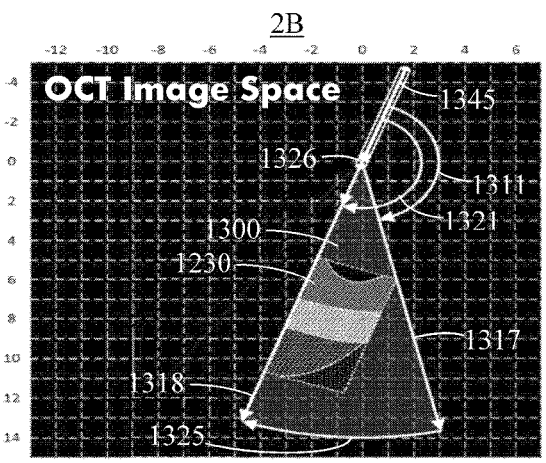
Figure 13:
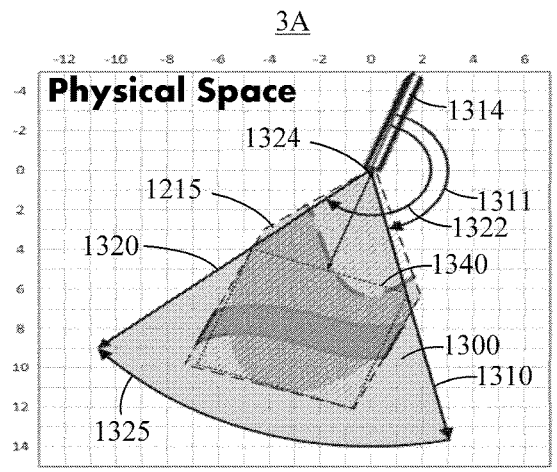
Figure 13:
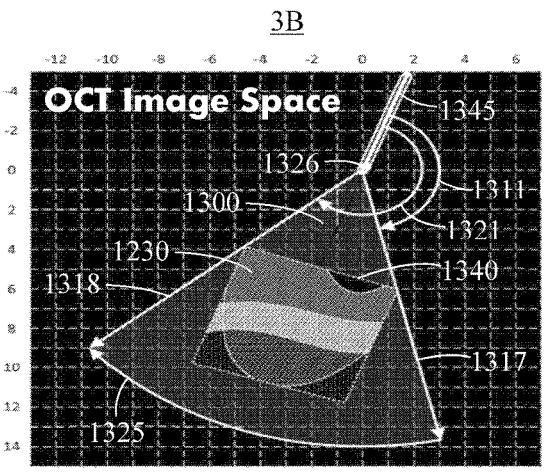

Continuing with the example illustrated in FIG. 12, FIG. 13 shows multiple diagrams depicting the acquisition of the OCT scan 1230 of the scanning area 1218 in both a physical and OCT image space. The top diagrams in FIG. 13 show the acquisition of A-scans starting with the first A-scan 1310 along the contour 1325 to the last A-scan 1320 within the volume 1300. Once acquired, each A-scan is subsequently generated in the OCT image space. In some instances this may be accomplished by setting an arbitrary reference origin in the OCT space to represent the position and direction of the interrogation point of the probe. This origin acts analogously to the common reference point as described in further detail above in that it couples the physical coordinate space with the OCT image space such that coordinates from one space may be transformed into the other. It should be noted that in some instances this point may be represented by more than one point and in other instances the set of more than one point may be an object. For example, in situations where both direction and position are needed to transform or generate the acquired A-scan in the OCT image space a phantom reference point may be defined such as the phantom 1345 comprising the reference point 1326 and a directional component used to establish the pitch, yaw, and role relative to the reference point. An alternate form that may also be used in the OCT space to provide a reference for direction may be to define a point having an associated 6 degrees of freedom inclusive of the positional coordinates (x, y, z) and the 3 directional coordinates (pitch, yaw, and roll).

In the present case shown in FIG. 13 the A-scan images may be generated relative to the reference origin along the same directions the A-scans were acquired relative to the interrogation point. For example, as shown in diagram 1A of FIG. 13 the direction 1311 relative to the interrogation point 1324 of the acquired 1D A-scan 1310 may be used to generate the 1D A-scans image 1317 by setting the image to have the same direction 1311 relative to the reference origin 1326. In this way the reference origin 1326 acts as an equivalent point to the interrogation point 1324 in that all the acquired A-scan image positions may be mapped relative to this point in the same spatial orientation in which they were acquired relative to the interrogation point. Thus allowing the A-scans to be spatially mapped to the OCT Space and form a coherent image via their amalgamation into a C-scan.

Continuing with the example provided in FIG. 13, it is apparent that as the A-scans are continuously acquired along contour 1325 in the physical space, that the OCT image 1230 is correspondingly built in the OCT image space. As per the figure, A-scan 1310 and corresponding image 1317 represent the first acquired A-scan of the OCT scan while A-scan 1320 and corresponding image 1318 represent the last acquired scans in each of the diagrams indicated by suffix's A-C. As the surgical area of interest 1215 is scanned via probe 1314 its OCT image 1230 is developed in the OCT image space. Given the spatial correspondence between the interrogation point 1324 of the OCT image probe 1314 and the reference point 1326, in some instances a spatial transform may be derived to align the OCT image relative to the position of the interrogation point in the same spatial position as the area that the OCT probe scanned. It should be noted that although OCT image 1230 does not visualize the entire surgical area of interest 1215, this need not always be the case when producing the OCT image. This particular visualization was chosen as it is reflective of common OCT image visualization image processing techniques, wherein the entire image may be segmented to only include specific volumes such as the volume 1340 outlined in both the surgical area of interest 1215 and the OCT scan image 1300. To further elaborate the OCT image 1230 in the example provided is produced via the amalgamation of A-scan images 1317→1318 along contour 1325 in the OCT image space followed by spatially mapping them in the same spatial orientation in which they were acquired (i.e. 1310→1320 along contour 1325) in the physical space. Thus producing an OCT image 1230 representative of the surgical area of interest 1215. Furthermore as described above this image is related to the interrogation point of the probe via the spatial relationship between each point in the OCT image and the interrogation point relative to which they were mapped. Generally it is assumed that the OCT image is acquired while the OCT probe remains for the most part static allowing the final image to have a single transform that may be used to transform any of its image voxels into a space containing a point defined to be equivalent to the reference point 1326 in the OCT image space.

Once acquired such a 3D volumetric OCT image may be registered with the 3D scan of the patient such as shown at step 905 in FIG. 9 and subsequently stitched together 906 with images from the 3D scan 903 to provide an enhanced 3D image 907. To illustrate, referring back to FIG. 12, an exemplary diagram 1260 of a 3D image space is provided that contains a 3D imaging scan of a patient formed of the patient brain 1235 and the surrounding anatomy of the patient's head 1240. It should be noted that in general any 3D imaging scan of the patient anatomy may be visualized in the image space and need not be segmented into portions such as the one shown. The segmented image is provided as it is common, in the neurosurgical space at least, to segment and in some cases (as will be seen below) strip the surrounding anatomy of the patient to reduce occlusion of important areas of interest, such as the brain. Nonetheless similar to the cross-sectional diagram of the patient 1250 this figure shows a region of the surgical area of interest magnified via box 1220, and further magnified via box 1218, which shows an exemplary OCT scan 1230 of the surgical area of interest 1215 acquired via an imaging probe 1102. As can be seen from the figure (more apparent in magnified box 1220) the OCT scan 1230 is stitched into the 3D imaging scan 1235 of the patient. This may provide benefit to the surgeon as an OCT scan may in some cases be of higher resolution then the 3D imaging scan of the patient in addition to being acquired intraoperatively and thus likely, more recently then the 3D imaging scan which is generally acquired preoperatively. It should be noted that although in the majority of cases the 3D imaging scan used for registration is a preoperative scan of the patient this should not be taken to limit the embodiments as disclosed herein to exclude scans which are acquired during the procedure itself. Furthermore although the 3D imaging scan used in the example in FIG. 12 is spatially registered with the patient other scans having different types of spatial correspondence or alternate correspondence metrics with the patient or spatially registered image of the patient may also be stitched with the OCT image.

In an embodiment the stitching of the OCT image may be accomplished using spatial transformations. One such transformation would be to stitch the OCT image into the 3D image of the patient using the position of the probe, known relative to both the 3D image and the OCT image. As described above when the 3D imaging of the patient in image space is registered with the patient in physical space the position of any tracked tool relative to the patient may be transformed into the image space relative to the spatially registered scan by applying the registration transform to the position of the tool in physical space, acquired via the tracking system. For example, as shown in FIG. 12 the position of the OCT probe 1102 and corresponding tracking markers 1210 may be transformed from the physical space containing the patient 1250 into the image space containing the 3D image of the patient 1260. This is shown in the image space 1260 by the tracking marker positions 1210 and their corresponding OCT probe visualization 1211 having a distal and proximal end, where in some embodiments the distal end may represent the position of the interrogation point from which the OCT image is acquired and, as discussed above, generated relative too.

Figure 14:
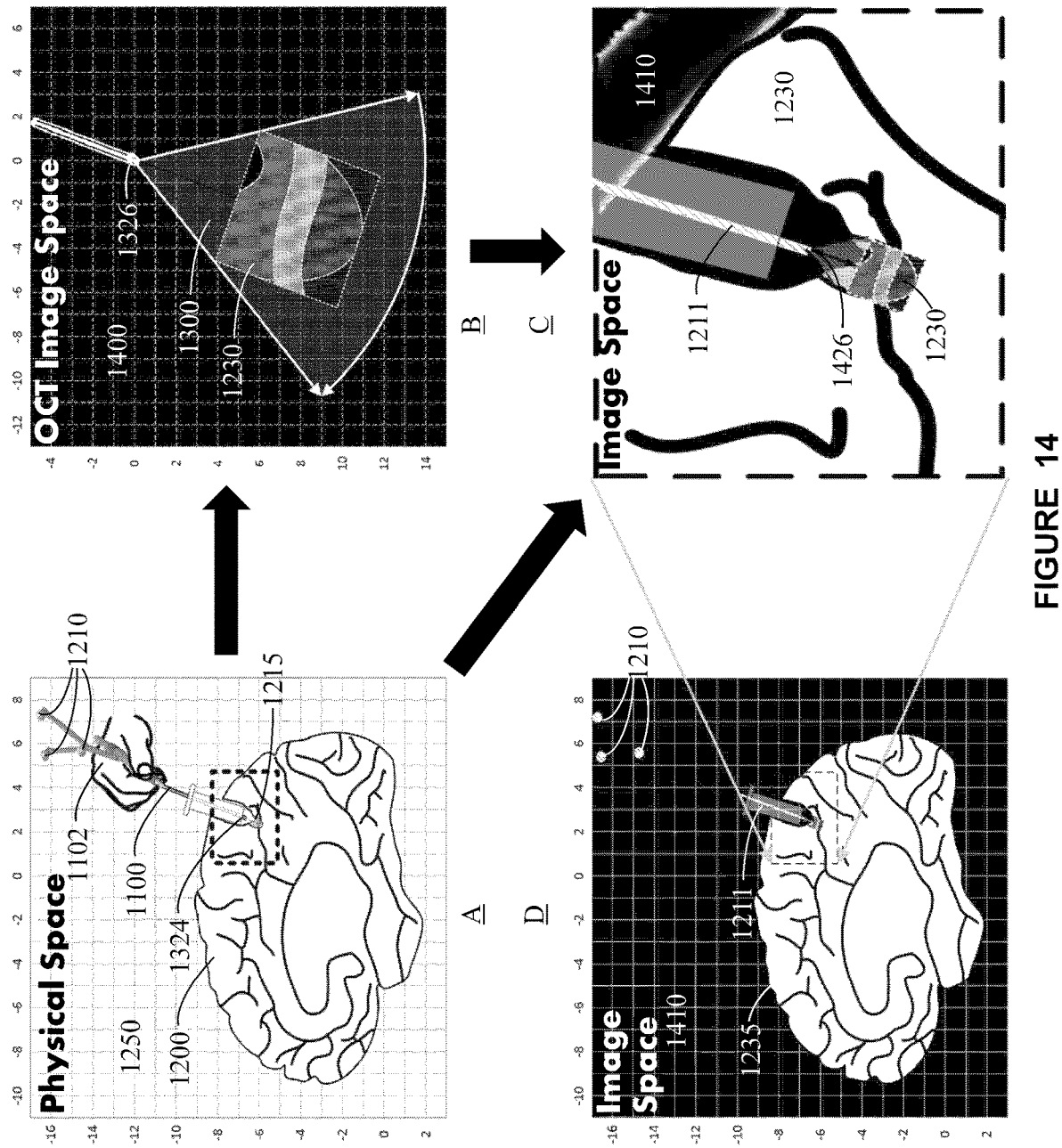
FIG. 14 is an alternate diagram showing the stitching of an OCT image into an image of a patient.

Referring to FIG. 14, the process of stitching (spatially mapping) the OCT image to the 3D image of the patient in the image space, containing the registered patient image, is further illustrated by way of exemplary diagrams, following the same examples as shown in FIG. 12 and FIG. 13. The first frame A in FIG. 14 follows from FIG. 12 and depicts the same cross sectional diagram 1250 of the patient in physical space, showing a user 1102 performing neurosurgery on a patient 1205, where the user is acquiring an internal OCT scan 1230 of the patient's brain 1200 within a surgical area of interest 1215, using an OCT probe 1100. The situation, shown in this frame, is more or less identical to that shown in FIG. 12, only that the patient's anatomy surrounding the anatomy of interest (the patient's brain) is stripped away for illustrative purposes. Thus, only the cross section of the brain is shown. The user, in this frame, is acquiring an OCT scan of the surgical area of interest 1215 with a tracked OCT probe 1100 having an interrogation point 1324 from which the A-scans are acquired and relative to which the A-scans' directions may be varied to scan an area of the patient's anatomy, as above described in further detail. This OCT scan is subsequently visualized as on the OCT image 1230 in the OCT image space 1400 as above described in further detail. Once completed, the OCT image 1230 in the OCT image space 1400 is spatially aligned relative to a common reference 1326. As above described, this common reference 1326 has a spatial correspondence with the interrogation point 1324 of the OCT probe 1100 in that the tissue imaged by the OCT scan has the same spatial relationship to the interrogation point 1324 as the OCT image of that tissue to the common reference 1326. As above described in further detail, the position of the OCT probe 1100 may be transformed into the image space 1410 by applying the registration transform to the tracking marker positions 1210 of the tracked OCT probe in physical space. Once transformed into image space, the positions of the tracking markers of the OCT probe 1100 may be used to infer the position of the interrogation point 1324 of the OCT probe as the interrogation point's position in physical space, determined relative to the tracking markers. Thus, this same spatial relation may be used to determine the interrogation point's position in the image space 1426 containing the 3D image of the patient

1230. The 3D image of the patient 1230, as shown in frame D, is, firstly, a cross section of the patient's anatomy and, secondly, is stripped of the image of the patient's surrounding anatomy to reduce occlusion of the tissue for a user visualizing this space to guide a surgical procedure. Once the interrogation point's position in the image space 1426 is known, the OCT image 1230 may be stitched into the 3D image 1230 of the patient by computing the registration transform from the position (in some instances inclusive of directional coordinates) of the common reference 1326 in the OCT image space 1400 to the position (in some instances inclusive of directional coordinates) of the interrogation point 1426 in the image space 1410. The computed transform may be derived using any suitable method known to skilled persons and generally should aim to minimize deviance between the common reference position and the interrogation point's position when imported into the image space 1410. Once computed, this transform may then be applied to the OCT image 1230 to import the OCT image 1230 into the image space and map the OCT image 1230 onto the 3D image of the patient 1235, as shown in frame C in FIG. 14. Once mapped, the surgeon may then use this mapped imaging to further enhance the guidance provided via the visualization of the image space 1410. All the explanatory figures, as disclosed herein used to illustrate the system as disclosed herein, need not be limited to two dimensions. Specifically, any references to figures or examples, describing any image interactions in two dimensions, should not be limited as such and may indeed be applied to any number of dimensions and may also be applied to produce the desired results as needed and intended by the disclosure herein.

Figure 15:
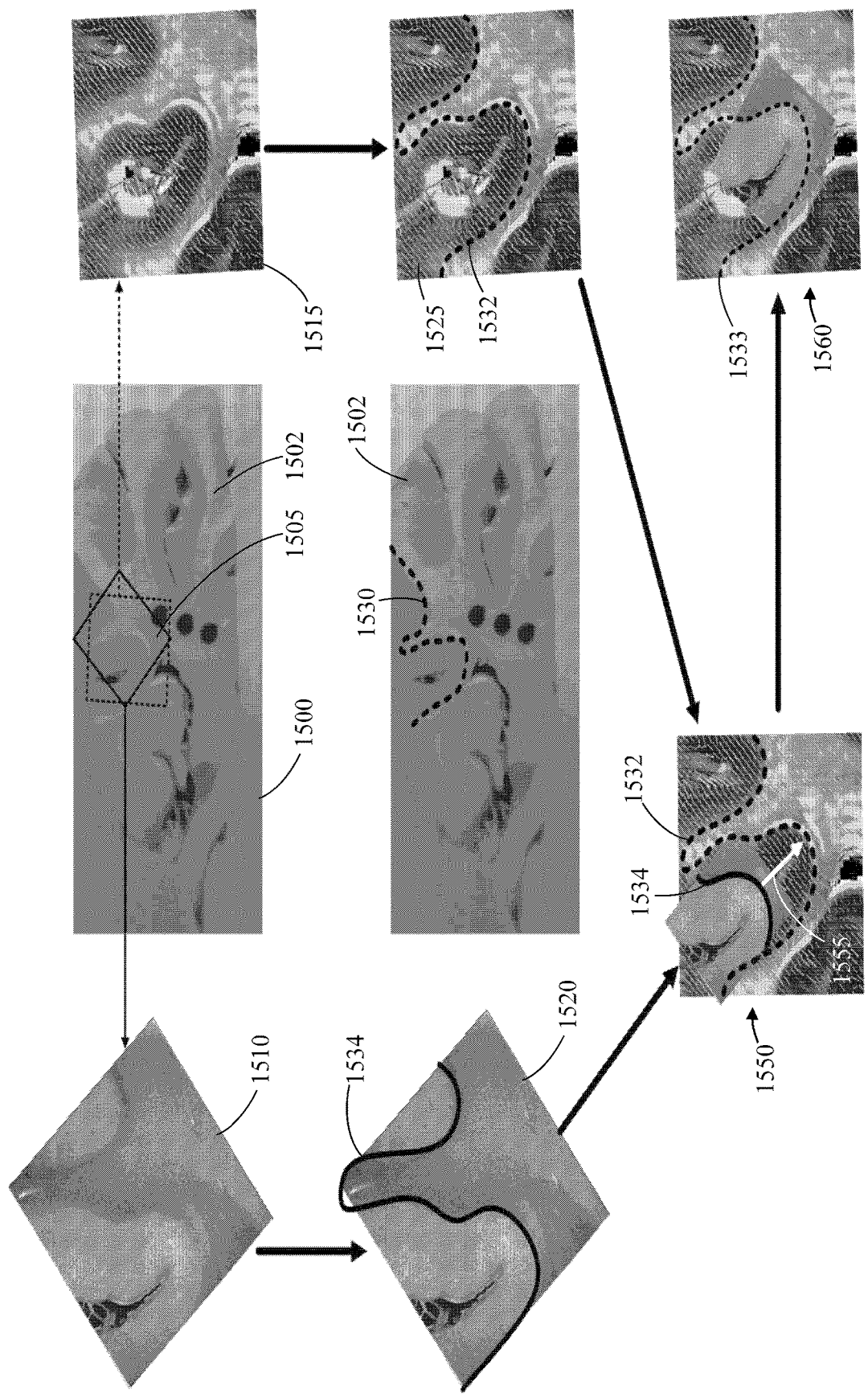
FIG. 15 is a diagram depicting the refinement of the stitching of an OCT image into a 3D image of the patient by feature mapping.

In some embodiments, after stitching the OCT image to the 3D image of the patient, the images may be further correlated by a processor that refines the registration of the images using feature matching methods. Given the multidimensional nature of the images where some may contain surface and subsurface features the processor may be used to refine the stitching (spatial mapping) of the OCT image in the 3D image of the patient by finding a refining transform that matches the surface and subsurface features of the OCT scan with the surface and subsurface features of the 3D image. Since the OCT image and 3D image of the patient are acquired in the same spatial vicinity in some instances there is likely similar features found in both images. For, example FIG. 15 shows a visible light image of a cross section view 1500 of an anatomy 1502, and two images of a portion 1505 of the anatomy, one taken using OCT 1510 and the other using an MRI scanner 1515. It is apparent from the figure that there exist boundary layers in the portion of the anatomy 1502 having unique feature shapes. In determining these features a processor such as the navigation system processor 302 may be programmed to extract these features from each image of the portion of the anatomy. More specifically given the boundary feature 1530 in the portion of the anatomy 1502 and reflected in both the OCT and MRI image of said portion, the processor may extract this features contours from each of the images as depicted by contours 1534 and 1532 respectively. Given the registration of the OCT scan with the MRI scan using spatial transformations via the positioning of the OCT probe relative to the patient, as described above, an example output is provided as 1550. It is apparent from this registration that there exists a misalignment (exaggerated for explanatory purposes) between the OCT scan and Mill scan of the portion. This misalignment may be revealed by the misalignment between the contours of the respective images 1534 and 1532 in the enhanced 3D image 1550. In such a case feature matching methods may be applied by the processor to refine the alignment of the OCT image 1510 with the 3D image of the patient 1515 in the enhanced image 1550 to produce a further enhanced 3D image. Upon computing such a refinement the processor may produce a transformation derived via feature mapping algorithms such as those known in the art and described below to refine the mapping (stitching) of the images. Such a refinement transform is shown as 1555 in the enhanced 3D image 1550. As is apparent from the figure this transformation attempts to align the contours 1534 and 1532 to minimize the Euclidean distances between them. Once the transformation is applied the processor may output a further enhanced 3D image as shown as 1560 in the figure. As can be seen in this new image the features of both the OCT image and Mill image are aligned correctly.

Feature matching algorithms that may be used to refine the mapping of the OCT images with the 3D images of the patient are known generally in the art. For example, it may be known that the registration of the pixels is accurate to, say, about 2 pixels widths of the 3D scanner image. In such a case, overlapping portions of the images may be correlated for example within +/−2 3D scanner pixel widths (so a 4 pixel square area in two dimensions) to determine an adjustment to the registration information. The accuracy of the adjustment may be significantly less than one pixel width, and may be less than the width of one pixel in the high resolution image. Correlation relies on the presence of distinguishable common features in overlapping parts of the images. The images can then be accurately aligned (e.g. by interpolation with sub-pixel accuracy) and stitched together. Generally the pixels in the 3D image will be replaced by the corresponding pixels in the high resolution scan, however other types of enhancements are also possible. For example, the images may be further processed to produce to interstich regions of high resolution depending on the needs of the user, while in other examples the images may be combined to produce a hybrid image.

Correlation relies on there being sufficient variation in the correlated portions so that common structures will correlate sufficiently well that a translation can be calculated. In some cases, there may not be enough variation in the overlapping portions of the images to permit a useful translation to be calculated, in which case the navigation system data could be used alone to register the images. Of course, where there is so little resolvable structure, small errors in the registration are of little or no consequence.

In general, after taking one OCT scan, which is incorporated into the enhanced 3D image, the position of the probe may be changed and another image of a different, but generally overlapping, sub-portion is taken. Note that the probe is not necessarily stationary while a scan is taken, and then moved only between scans, however, the images can be processed based on the known movements of the probe so that they provide the equivalent of such successive stationary scans. After the second OCT scan is obtained, it is then combined in a manner similar to the first scan with the enhanced 3D image to produce an updated enhanced 3D image which can be immediately displayed to the surgeon. This image is registered with the 3D scanner image data and stitched together with images from the 3D scanner to provide an enhanced 3D image. The registration can be performed in various ways, as discussed generally above. In some embodiments where the 3D scanner is moveable such as when using an ultrasound probe or a structured light scanner the position of the 3D scanner may be known via a tracking system or other applicable mechanism. For example, it may be fixed, or may be movable and tracked by the navigation system. The correspondence between pixels in the sub-portion of the 3D scanner image with pixels in the 3D scan can then be determined and the OCT image data stitched by a processor into the 3D scan of the patient. Optionally the images can be correlated by a processor to refine the registration of the images as described above in further detail.

In some embodiments, the 3D scanner and OCT scanner, may be combined in a handheld device. A surgeon may direct the device's scanners at a portion of a patient during surgery and vary the field of view and viewing angle of the device by moving it by hand. In one instance a 3D scanner, for example using structured light, scans the area being viewed and provides a 3D image of the corresponding portion of the patient's surface. The OCT scanner provides a high resolution scan of a sub-portion of the patient from the angle at which the device is held. The surgeon may vary the angle from which the OCT scanner is obtaining imagery so that the OCT scanner next scans substantially the same sub-portion of the patient, but from a different angle. The system may then combine two scans at different angles using stereoscopic analysis to produce a 3D visualization of the imaged sub-portion.

In general, after taking one OCT scan, which is incorporated into the enhanced 3D image, the position of the probe is changed and another image of a different, but generally overlapping, sub-portion is taken. Note that the probe is not necessarily stationary while a scan is taken, and then moved only between scans, however, the images can be processed based on the known movements of the probe so that they provide the equivalent of such successive stationary scans. After the second OCT scan is obtained, it is then combined in a manner similar to the first scan with the enhanced 3D image to produce an updated enhanced 3D image which can be immediately displayed to the surgeon. Although it is not necessarily the case, the second scan will generally overlap the first scan. In that case, when correlation is used, it will be, at least in part, the OCT data that is correlated in the overlapping regions of the two high resolutions scans, which provides a highly accurate registration of the images. For example, when the feature mapping algorithm is applied, it may be used to map the one or more OCT scans to one another as well as with the 3D scan. Furthermore the feature mapping algorithms implemented via the processor as described above may be extended to include the refinement of multiple overlapping or non-overlapping OCT scans as well as the 3D image of the patient in the enhanced 3D image to produce a further enhanced or updated 3D image.

It should be noted that, of course, registration of images is not limited to simple translations of the images, which in many cases may not be adequate (for example where the viewing angles of the imagers are varying significantly). In such cases, spatially varying translations, or other forms of image warping, may be used to rectify an image prior to stitching it into the updated enhanced 3D image. Such techniques are well known to skilled persons.

The results of the stereoscopic analysis to refine the accuracy of the contour lines. In addition, birefringence data such as retardation values and orientation values can be more accurately calculated from multi-angle measurements. This may be done, for example, using methods such as those described in Kasaragod et al., "Experimental validation of an extended Jones matrix calculus model to study the 3D structural orientation of the collagen fibers in articular cartilage using polarization-sensitive optical coherence tomography," Biomed. Opt. Exp. 3(3), 378 (2012).

The OCT imager also provides depth information for the surface points imaged in the sub-portion of the imaged portion of the patient. Such depth information is generally more accurate than that provided by the 3D scanner, such as when using a CT, MRI, or US scanner, and so is used to refine the depth contours in the sub-portion. For example, the contours in the sub-portion may be derived entirely from the OCT scanner in the internal portion of the sub-portion, and then adjusted as required near the boundaries of the sub-portion to ensure continuity with the contours outside the sub-portion. Alternatively, some blending of the depth information provided by the two imaging systems may be performed, with the values provided by the 3D scanner being given more weight closer to the boundaries of the sub-portion.

The enhanced 3D image is then displayed on a monitor visible to the surgeon. The system may provide the surgeon with options to manipulate the image, such as to zoom in on portions or perform three dimensional movements.

In the primary enhanced 3D image of the patient shown to the surgeon, there may be some indication provided that sub-surface imagery is available in the sub-portions scanned by the high resolution imager. The surgeon may be provided the option to view sub-surface image data, which may be presented on the same display or on a different display. For example, the surgeon may specify a plane (or the system may use a default plane, e.g. parallel to the central portion of the surface in the sub-portion) and then the system may display an image slice in that plane, and possibly also for an orthogonal plane. The surgeon may then be able to, for example, vary the depth of one of the planes. 3D views of sub-surface structures may also be rendered by the processor and made available to the surgeon.

In some embodiments the 3D scanner may be a structured light scanner and in those cases a surface image of the patient may be acquired as opposed to a full volumetric image. In these cases the OCT scan may be stitched to the surface through registration methods used to best fit the surface as derived from the OCT scan with the surface of the patient as acquired via the 3D structured light scanner. Such methods may include for example minimizing a Euclidean distance between the surface feature extracted from the OCT image and the surface provided from the patient image. For a surface image derived from the OCT scan, only the initial reflections are required. These points may be used to form a point cloud array of voxels where a depth value (based on reflection time) is associated with each voxel and in some embodiments the voxels may be extrapolated to form a surface. In some instances the surface may be fitted via an iterative cost minimization algorithm. In one example, the iterative cost minimization function may take the form of an Iterative Closest Point (ICP) approach to calculate the registration transformation, such as that detailed in "A Method for Registration of 3-D Shapes" by Paul J. Besl and Neil D. McKay, IEEE Transactions on Pattern Analysis and Machine Intelligence, pp. 239-256, VOL. 14, No. 2, February 1992, the entirety of which is hereby incorporated by reference. However, any suitable approach may be used depending on the design criteria of a particular application.

Generally, a computer, computer system, computing device, client or server, as will be well understood by a person skilled in the art, includes one or more than one electronic computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. It is the express intent of the inventors that a "processor" does not include a human; rather it is limited to be an electronic device, or devices, that perform digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.) Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

It is intended that the invention includes computer-readable memory containing any or all of the software described herein. In particular, the invention includes such software stored on non-volatile computer-readable memory that may be used to distribute or sell embodiments of the invention or parts thereof.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

We claim:

1. A method of optical coherence tomography (OCT) image acquisition, using a computer processor, an OCT imaging system, a three dimensional imaging system and a navigation system, to provide a three dimensional visual representation of a patient intraoperatively, the patient having a surface and having discernable surface features and subsurface features, the method comprising:

acquiring a three dimensional imaging scan of an in vivo portion of the surface of the patient using the three dimensional imaging system;

registering the three dimensional imaging scan of the in vivo portion of the patient with the patient intraoperatively;

acquiring a first OCT imaging scan covering a first sub-portion of the in vivo portion of the patient using the OCT imaging system, the OCT imaging system tracked by the navigation system;

acquiring a second OCT imaging scan covering a second sub-portion of the in vivo portion of the patient using the OCT imaging system;

warping at least one of the first OCT imaging scan, the second OCT imaging scan, and the three dimensional imaging scan to refine registration thereof;

stitching, together, the first OCT imaging scan and the second OCT imaging scan using a stitching algorithm to produce an amalgamated OCT image;

correlating the first OCT imaging scan and the second OCT imaging scan with the three dimensional imaging scan by finding and applying a refining transform that matches the discernable surface and subsurface features of the first OCT imaging scan and the second OCT imaging scan with the discernable surface and subsurface features of the 3D image to refine registration thereof;

combining the three dimensional imaging scan and the amalgamated OCT image to create an enhanced three dimensional image of the in vivo portion of the patient; and effecting display of the enhanced three dimensional image by a display device in real time, wherein stitching comprises:

applying a registration transform to a plurality of tracking marker positions of a tracked OCT probe in a physical space, thereby providing an image space of the plurality of tracking marker positions;

determining an interrogation point position of the tracked OCT probe in the physical space using the plurality of tracking marker positions;

determining an interrogation point position of the tracked OCT probe in the image space using the plurality of tracking marker positions;

stripping the three dimensional imaging scan of surrounding anatomy to reduce occlusion therein;

computing the registration transform from a position of a common reference in an OCT image space to the interrogation point position of the tracked OCT probe in the image space;

applying the registration transform to the first OCT imaging scan, thereby importing the first OCT imaging scan into the image space; and mapping the first OCT imaging scan onto the three dimensional imaging scan, wherein at least one of applying the registration transform to the plurality of tracking marker positions and applying the registration transform to the first OCT imaging scan comprises at least one of:

minimizing a Euclidean distance between a surface feature extracted from the first OCT image and a surface of the three dimensional imaging scan;

extrapolating a plurality of voxels from a point cloud array of voxels, wherein a depth value, based on a reflection time, is associated with each voxel in the point cloud array of voxels; and fitting the surface of the three dimensional imaging scan by using an iterative cost minimization algorithm, using the iterative cost minimization algorithm comprising using an iterative closest point (ICP) technique, and wherein the three dimensional imaging system comprises at least one of a magnetic resonance imaging device and a stereoscopic camera using photometric imaging and geometric imaging.

2. The method of claim 1, wherein combining the three dimensional imaging scan and the amalgamated OCT image comprises forming a spatial correspondence between the amalgamated OCT image and the registered three dimensional image of the patient.

3. The method of claim 1, further comprising:

acquiring a subsequent OCT imaging scan covering a subsequent sub-portion of the in vivo portion of the patient using the OCT imaging system;

stitching together a previous OCT imaging scan and the subsequent OCT imaging scan using the stitching algorithm to produce a subsequent amalgamated OCT image;

combining the three dimensional imaging scan and the subsequent amalgamated OCT image to create a subsequent enhanced three dimensional image of the in vivo portion of the patient;

updating the subsequent enhanced three dimensional image; and effecting display of the subsequent enhanced three dimensional image by a display device in real-time.

4. The method of claim 1, further comprising displaying the enhanced three dimensional image.

5. The method of claim 1, wherein stitching the OCT imaging scans comprises correlating overlapping portions of the OCT imaging scans to identify common features in the two OCT imaging scans by the computer processor.

6. The method of claim 5, wherein the common features in the OCT imaging scans comprise one or more subsurface features.

7. The method of claim 1, wherein combining the three dimensional imaging scan and the amalgamated OCT image is performed such that pixels, in the three dimensional imaging scan that correspond to locations in the sub-portions covered by the amalgamated OCT image, are replaced by values derived from the amalgamated OCT image.

8. The method of claim 1, wherein the three dimensional imaging system is also tracked by the navigation system.

9. The method of claim 1, wherein the three dimensional imaging system comprises a structured light camera, and wherein the three dimensional imaging system employs structured light.

10. The method of claim 1, wherein the three dimensional imaging system outputs a 3D contour scan image.

11. The method of claim 1, wherein the OCT imaging scans are formed from a plurality of B-scans.

12. An image acquisition system for providing a three dimensional visual representation of a patient intraoperatively, the patient having a surface and having discernable surface and subsurface features, the system comprising:

an OCT imaging system;

a three dimensional imaging system;

a navigation system; and a computer processor configured to:

acquire a three dimensional imaging scan of an in vivo portion of the surface of the patient using the three dimensional imaging system;

register the three dimensional imaging scan of the in vivo portion of the patient with the patient intraoperatively;

acquire a first OCT imaging scan covering a first sub-portion of the in vivo portion of the patient using the OCT imaging system, the OCT imaging system tracked by the navigation system;

acquire a second OCT imaging scan covering a second sub-portion of the in vivo portion of the patient using the OCT imaging system;

warp at least one of the first OCT imaging scan, the second OCT imaging scan, and the three dimensional imaging scan to refine registration thereof;

stitch, together, the first OCT imaging scan and the second OCT imaging scan using a stitching algorithm to produce an amalgamated OCT image;

correlate the first OCT imaging scan and the second OCT imaging scan with the three dimensional imaging scan by finding and applying a refining transform that matches the discernable surface and subsurface features of the first OCT imaging scan and the second OCT imaging scan with the discernable surface and subsurface features of the 3D image to refine registration thereof;

combine the three dimensional imaging scan and the amalgamated OCT image to create an enhanced three dimensional image of the in vivo portion of the patient; and effect display of the enhanced three dimensional image by a display device in real time, wherein the computer processor is configured to stitch, together, the first OCT imaging scan and the second OCT imaging scan by:

applying a registration transform to a plurality of tracking marker positions of a tracked OCT probe in a physical space, thereby providing an image space of the plurality of tracking marker positions;

determining an interrogation point position of the tracked OCT probe in the physical space using the plurality of tracking marker positions;

determining an interrogation point position of the tracked OCT probe in the image space using the plurality of tracking marker positions;

stripping the three dimensional imaging scan of surrounding anatomy to reduce occlusion therein;

computing the registration transform from a position of a common reference in an OCT image space to the interrogation point position of the tracked OCT probe in the image space;

applying the registration transform to the first OCT imaging scan, thereby importing the first OCT imaging scan into the image space; and mapping the first OCT imaging scan onto the three dimensional imaging scan, wherein at least one of applying the registration transform to the plurality of tracking marker positions and applying the registration transform to the first OCT imaging scan comprises at least one of:

minimizing a Euclidean distance between a surface feature extracted from the first OCT image and a surface of the three dimensional imaging scan;

extrapolating a plurality of voxels from a point cloud array of voxels, wherein a depth value, based on a reflection time, is associated with each voxel in the point cloud array of voxels; and fitting the surface of the three dimensional imaging scan by using an iterative cost minimization algorithm, using the iterative cost minimization algorithm comprising using an iterative closest point (ICP) technique, and wherein the three dimensional imaging system comprises at least one of a magnetic resonance imaging device and a stereoscopic camera using photometric imaging and geometric imaging.

13. The system of claim 12, wherein combining the three dimensional imaging scan and the amalgamated OCT image comprises forming a spatial correspondence between the amalgamated OCT image and the registered three dimensional image of the patient.

14. The system of claim 12, wherein the computer processor is further configured to:

acquire a subsequent OCT imaging scan covering a subsequent sub-portion of the in vivo portion of the patient using the OCT imaging system;

stitch together a previous OCT imaging scan and the subsequent OCT imaging scan using the stitching algorithm to produce a subsequent amalgamated OCT image;

combine the three dimensional imaging scan and the subsequent amalgamated OCT image to create a subsequent enhanced three dimensional image of the in vivo portion of the patient;

update the subsequent enhanced three dimensional image; and effect display of the subsequent enhanced three dimensional image via a display device in real-time.

15. The system of claim 12, wherein the computer processor is configured to stitch the OCT imaging scans by correlating overlapping portions of the OCT imaging scans to identify common features in the two OCT imaging scans.

16. The system of claim 15, wherein the common features in the OCT imaging scans comprise one or more subsurface features.

17. The system of claim 12, wherein the computer processor is configured to combine the three dimensional imaging scan and the amalgamated OCT image is done so such that pixels, in the three dimensional imaging scan that correspond to locations in the sub-portions covered by the amalgamated OCT image, are replaced by values derived from the amalgamated OCT image.

18. The system of claim 12, wherein the three dimensional imaging system is also tracked by the navigation system.

19. The system of claim 12, wherein the three dimensional imaging system comprises a structured light camera, and wherein the three dimensional imaging system employs structured light.

20. The system of claim 12, wherein the three dimensional imaging system outputs a 3D contour scan image.

* * * * *